(12) United States Patent
Valle et al.

(10) Patent No.: US 6,962,794 B2
(45) Date of Patent: Nov. 8, 2005

(54) APPLICATION OF GLUCOSE TRANSPORT MUTANTS FOR PRODUCTION OF AROMATIC PATHWAY COMPOUNDS

(75) Inventors: Fernando Valle, Cuernavaca (MX); Noemi Mejia, Cuernavaca (MX); Alan Berry, Belmont, CA (US)

(73) Assignees: Genecor International, Inc., Palo Alto, CA (US); Universidad Nacional Autonoma de Mexico, Coyoacan (MX)

(*) Notice: Subject to any disclaimer, the term of this patent is extended or adjusted under 35 U.S.C. 154(b) by 573 days.

(21) Appl. No.: 08/940,692

(22) Filed: Sep. 30, 1997

(65) Prior Publication Data

US 2002/0155521 A1 Oct. 24, 2002

Related U.S. Application Data

(63) Continuation of application No. 08/435,510, filed on May 5, 1995, now abandoned.

(51) Int. Cl.[7] ............................ C12N 1/00; C12N 1/21; C12N 15/01; C12N 15/09; C12P 13/22
(52) U.S. Cl. ........................ 435/41; 435/440; 435/471; 435/108; 435/243; 435/813; 435/252.3; 435/252.33; 435/252.1
(58) Field of Search ................................ 435/440, 471, 435/41, 108, 243, 813, 252.8, 252.3, 252.33, 252.1

(56) References Cited

U.S. PATENT DOCUMENTS

| | | | |
|---|---|---|---|
| 4,520,103 A | | 5/1985 | Ensley, Jr. ................... 435/121 |
| 5,168,056 A | * | 12/1992 | Frost ....................... 435/172.3 |
| 5,169,768 A | | 12/1992 | Backman .................... 435/108 |
| 5,272,073 A | | 12/1993 | Frost et al. ................. 435/155 |
| 5,602,030 A | * | 2/1997 | Ingrahm et al. .......... 435/252.3 |

FOREIGN PATENT DOCUMENTS

| WO | 87/01130 | 2/1987 |
|---|---|---|

OTHER PUBLICATIONS

W.H. Holms, "The Central Metabolic Pathways of *Escherichia coli*: Relationship Between Flux and Control at a Branch Point, Efficiency of Conversion to Biomass, and Excretion of Acetate", Curr. Topics Cell. Regulation. 28: 69–105, 1986.*
F. Biville et al., "Mutants of *Escherichia coli* Producing Pyrroloquinoline Quinone", J. Gen. Microbiol. 137: 1775–1782, 1991.*
M.H. Saier et al., "Characterization of Constitutive Galactose Permease Mutants in *Salmonella typhimurium*", J. Bacteriol. 113(1): 512–514, Jan. 1973.*
Mori et al., "Pyruvate formation and sugar metabolism in an amino acid–producing bacterium *Brevibacterium flavum*," Agric. Biol. Chem. 51:129–138 (1987).

Miller et al., "Production of phenylalanine and organic acids by phosphoenolpyruvate carboxylase–deficient mutants of *Escherichia coli*," J. Ind. Microbiol. 2:143–149 (1987).
Lida et al., "Identification and characterization of the tktB gene encoding a second transketolase in *Escherichia coli* K–12," J. Bacteriol. 175:5375–5383 (1993).
Holms, W. "The central metabolic pathways of *Escherichia coli*: relationship between flux and control at a branch point, efficiency of conversion to biomass, and excretion of acetate," In: Current Topics in Cellular Regulation, 28:69–105 (1986) Academic Press, New York.
Draths et al., "Synthesis using plasmid–based catalysis: Plasmid assembly and 3–deoxy–D–arabino–heptulosonate production," J. Am. Chem. Soc. 112:1657–1659 (1990).
Postma et al., "Phosphoenolpyruvate carbohydrate phosphotransferase systems of bacteria," Microbiol. Rev. 57:543–594 (1993).
Romano et al., "Distribution of the phosphoenolpyruvate: glucose phosphotransferase system in fermentative bacteria," J. Bacteriol. 139: 93–97 (1979).
Saier et al., "Energetics of the bacterial phosphotransferase system in sugar transport and the regulation of carbon metabolism," In: Bacterial energetics, 273–299, T.A. Krulwich, ed., Academic Press, New York.
Varma et al., "Biochemical production capabilities of *Escherichia coli*," Biotech and Bioengin. 42: 59–73 (1993).
Navas–Castillo et al., "Evidence for a phosphoenolpyruvate dependent sugar–phosphotransferase system in the mollicute *Acholeplasma florum*" Biochimie (Paris) 75: 675–679 (1993).
Wagner et al., "Cloning and characterization of the scrA gene encoding the sucrose–specific enzyme II of the phosphotransferase system from *Staphylococcus Xylosus*," Mol. Gen. Genet. 241: 33–41 (1993).
Meadow et al., "The bacterial phosphoenolpyruvate: glycose phosphotransferase system," Annu Rev. Biochem. 59:497 542 (1990).
Chen et al., "Sequence analysis of scrA and scrB from *Streptococcus sobrinus* 6715" Infect. Immun. 61: 2602–2610 (1993).

(Continued)

*Primary Examiner*—Rebecca E. Prouty
(74) *Attorney, Agent, or Firm*—Genencor International, Inc.

(57) ABSTRACT

This invention describes methods for enhancing carbon flow into a pathway of a host cell to enhance the biosynthetic production of compounds therefrom, the host cells being selected based on being phenotypically Pts[-]/glucose[+]. Such host cells are capable of transporting glucose without consuming PEP, resulting in conservation of PEP which can be re-directed into the pathway in order to enhance the production of desired compounds along the pathway. Pts[-]/glucose[+] mutants have been shown to be advantageous for the enhanced production of the aromatic amino acids.

25 Claims, 7 Drawing Sheets

OTHER PUBLICATIONS

Cocaign et al., "Batch kinetics of *Corynebacterium glutamicum* during growth on various carbon substrates: use of substrate mixtures to localise metabolic bottlenecks," Appl. Microbiol. and Biotechnol. 40:526–530 (1993).

Yoon et al., "Cloning and characterization of the gene encoding enzyme II of the *Brevibacterium lactofermentum* phosphoenolpyruvate–dependent sugar phosphotransferase system," Abst. Ann. Meet. Am. Soc. Microbiol. 0–25 (1993).

Degnan et al., "Transport and metabolism of glucose and arabinose in *Bifidobacterium breve*," Arch. Microbiol. 160:144–151 (1993).

Chattopadhyay et al., "*Azospirillum brasilense* locus coding for phosphoenolpyruvate fructose phosphotransferase system and global regulation of carbohydrate metabolism," J. Bacteriol. 175:3240–3243 (1993).

Mitchell et al., "Identification of a phosphoenolpyruvate fructose phosphotransferase system (fructose 1–phosphate forming) in Listeria Monocytogenes," J. Bacteriol. 175: 2758–2761 (1993).

Benthin et al., "Transport of sugars via two anomer–specific sites on mannose–phosphotransferase system in *Lactococcus cremoris*: in vivo study of mechanism kinetics and adaptation," Biotechnol. Bioeng. 42: 440–448 (1993).

Yu et al., "Chemotaxis of the marine bacterium *Vibrio furnissii* to sugars: a potential mechanism for initiating the catabolic cascade," J. Biol. Chem. 268: 9405–9409 (1993).

Henderson et al., "Homologous sugar transport proteins in *Escherichia coli* and their relatives in both prokaryotes and eukaryotes," Philos. Trans. R. Soc., London, 326(1236): 391–410 (1990).

Weickert et al., "The galactose regulon of *Escherichia coli*," Molecular Microbiol. 10: 245–251 (1993).

Postma, P. "Phosphotransferase system for glucose and other sugars," In: *Escherichia coli* and *Salmonella Typhimurium*, Cellular and Molecular Biology, 127–141, F. Neidhardt, J. Ingraham, K. Low, M. Schaechter and J. Umbarger, ed.) ASM Publications, Washington, D.C. (1987).

Biville et al., "Mutants of *Escherichia coli* producing pyrroloquinoline quinone," J. Gen. Microbiol. 137: 1775–1782 (1991).

Saier et al., Characterization of constitutive galactose permease mutants in *Salmonella typhimurium*, J. Bacteriol. 113: 512–514 (1973).

Silhavy et al., In: Experiments with Gene Fusions, 110–112, Cold Springs Harbor Laboratory, New York. (1984).

Levy et al., "Cyclic AMP synthesis in *Escherichia coli* strains bearing known deletions in the pts phosphotransferase operon," Gene 86:27–33 (1990).

Cordaro et al., "Fosfomycin resistance: selection method for internal and extended deletions of the phosphoenolpyruvate: sugar phosphotransferase genes of *Salmonella typhimurium*," J. Bacteriol. 128: 785–793 (1976).

Dykhuizen et al., "Selection in chemostats," Microbiol. Rev. 47:150–168 (1983).

Yanisch–Perron et al., "Improved M13 phage cloning vectors and host strains: nucleotide sequence of the M13mp18 and pUC19 vectors," Gene 33: 103–119 (1985).

Weickert et al., "Control of transcription of gal repressor and isorepressor genes in *Escherichia coli*," J. Bacteriol. 175: 251–258 (1993).

Backman et al., "Construction of Plasmids carrying the cI gene of bacteriophage λ," Proc. Natl. Acad. Sci. 73:4174–4178 (1976).

Srinivasan et al., "2–keto–3–deoxy–D–arabo–heptonic acid 7–phosphate synthetase," J. Biol. Chem. 234: 716–722 (1959).

* cited by examiner

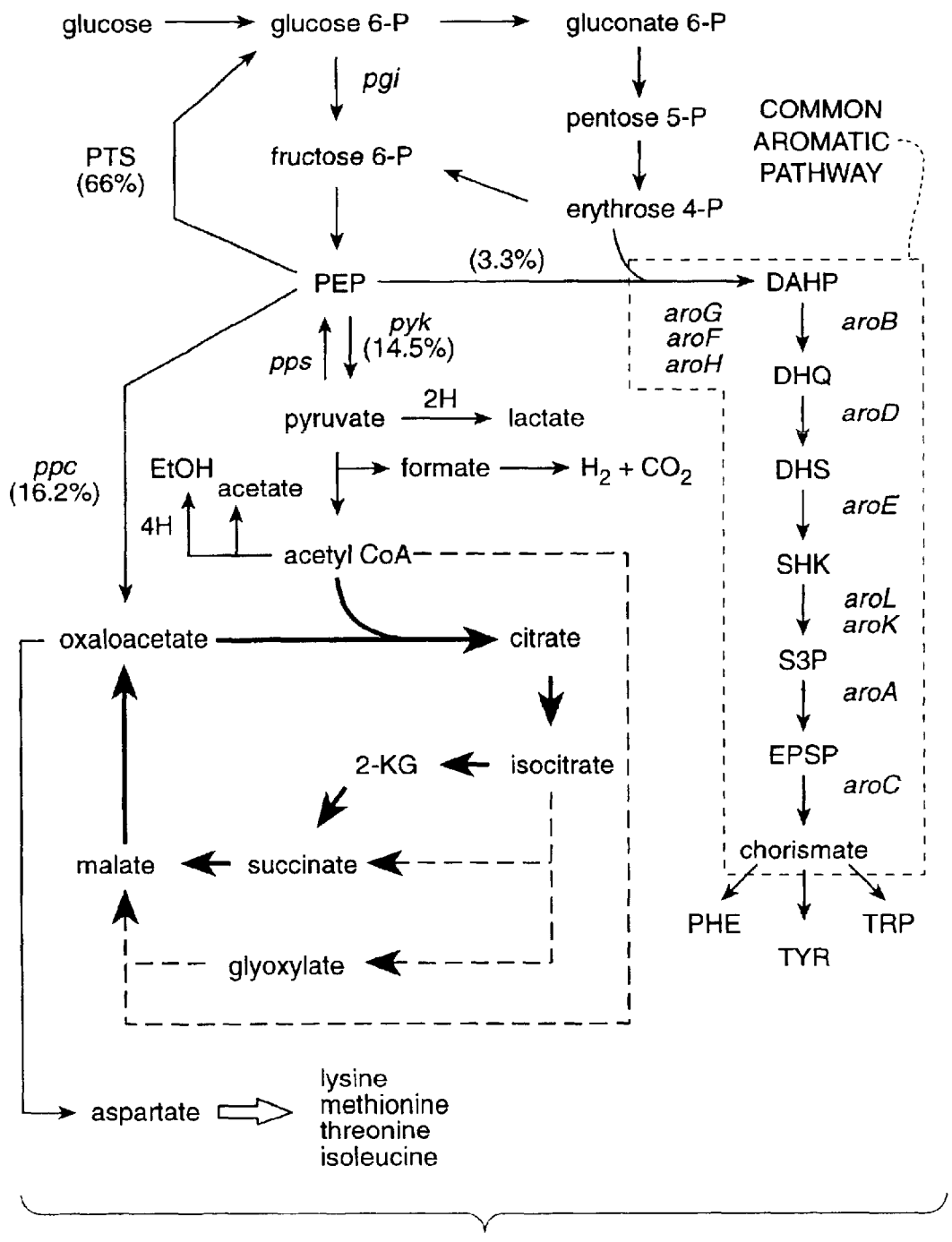
FIG._1

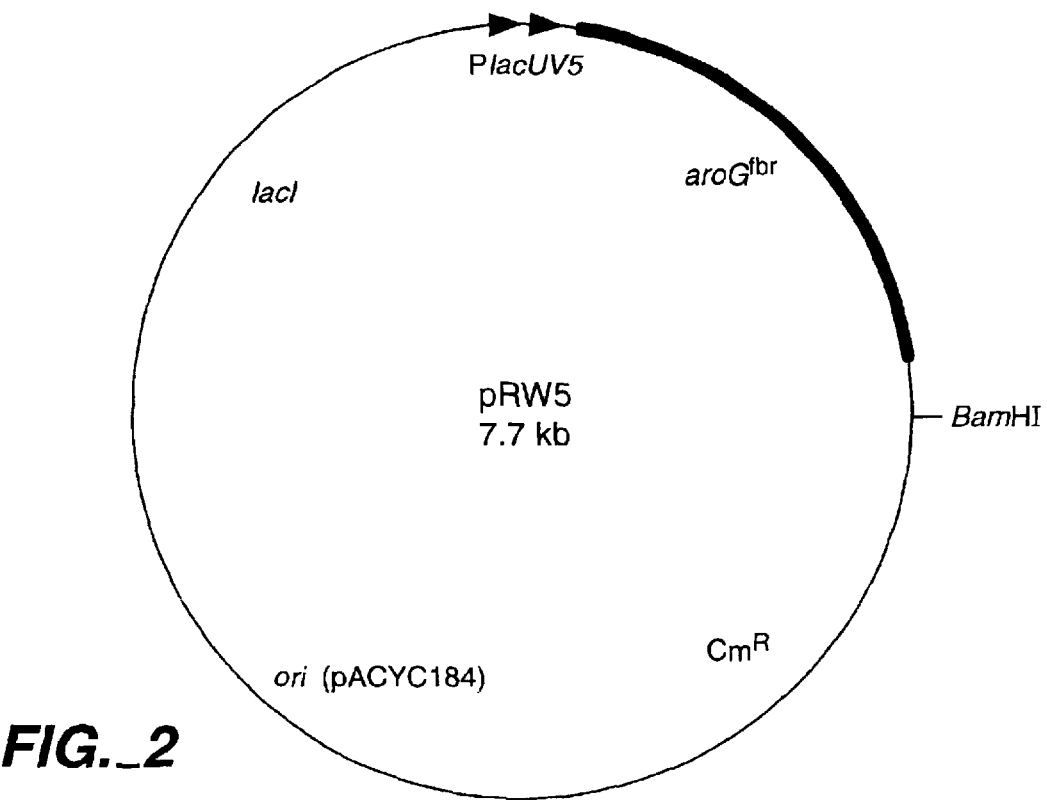
FIG._2
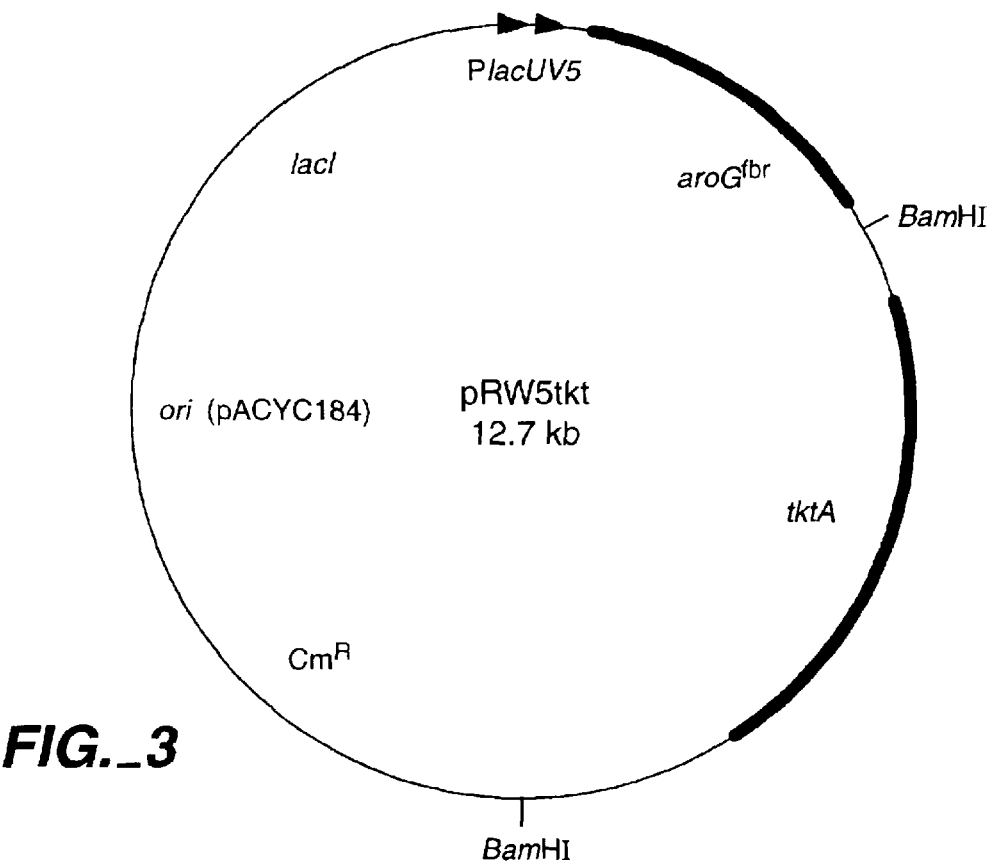
FIG._3

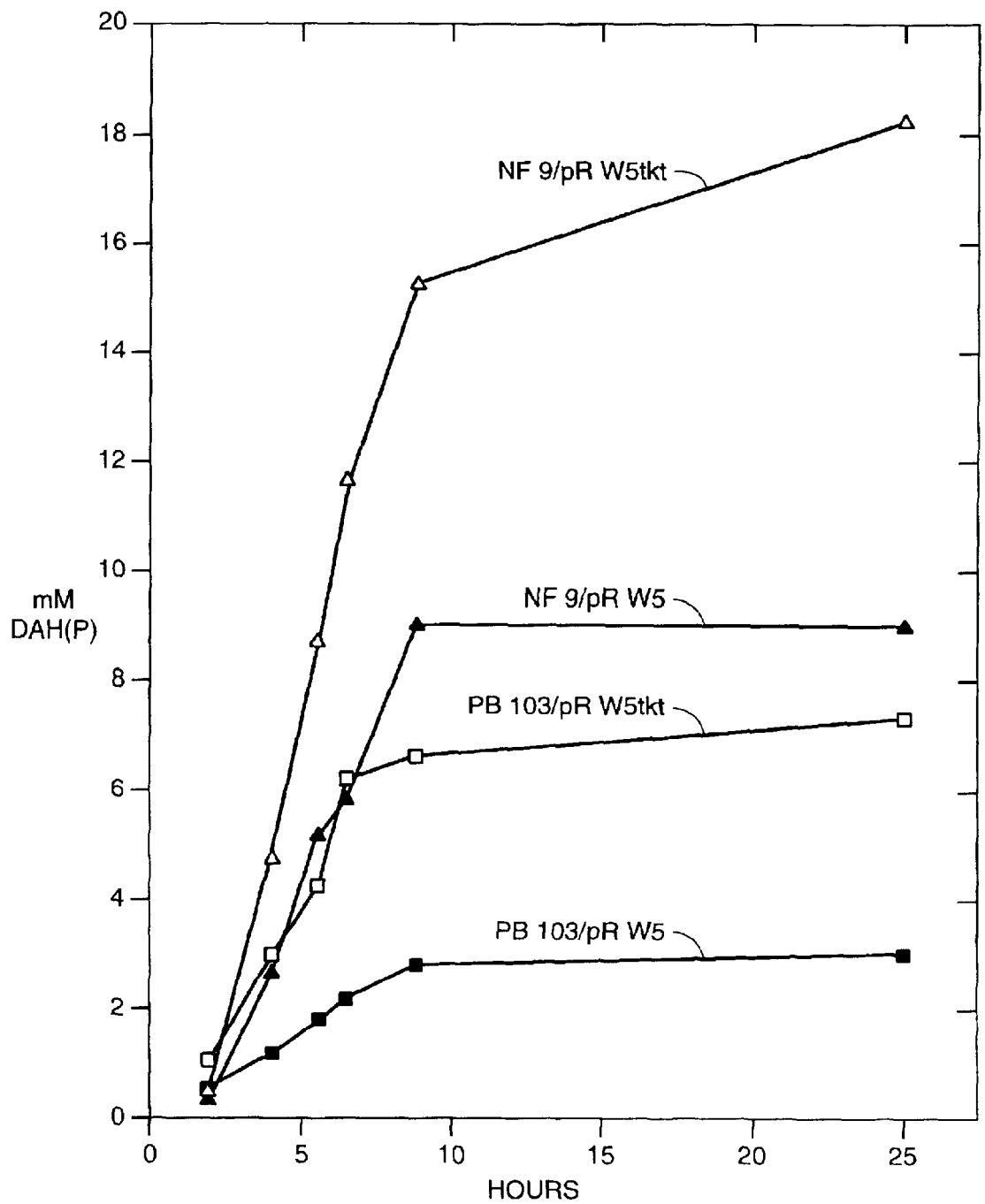
FIG._4

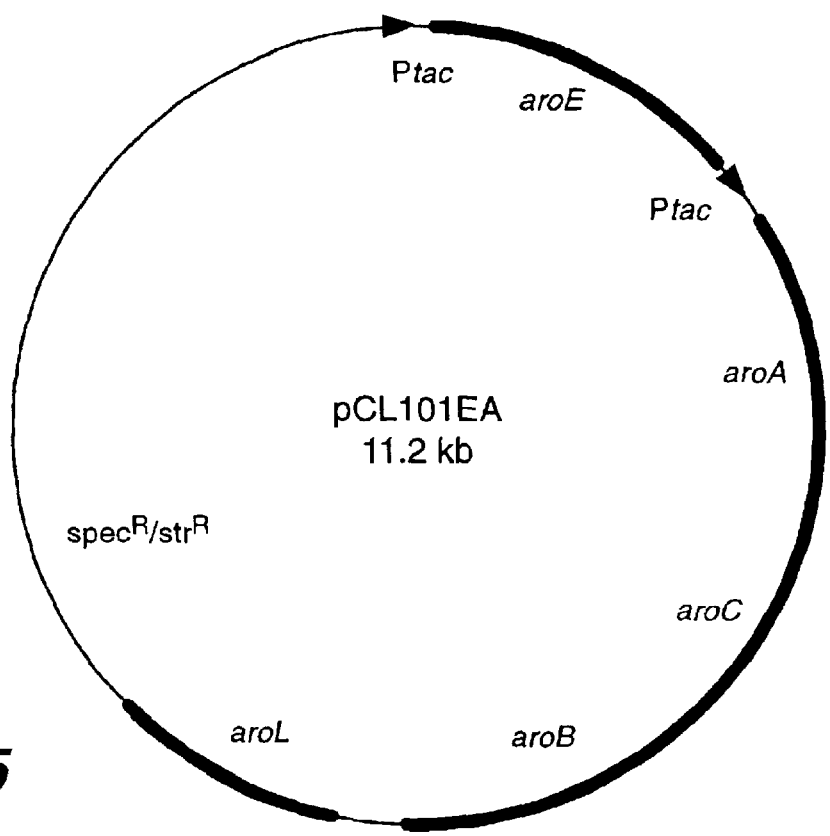
FIG._5
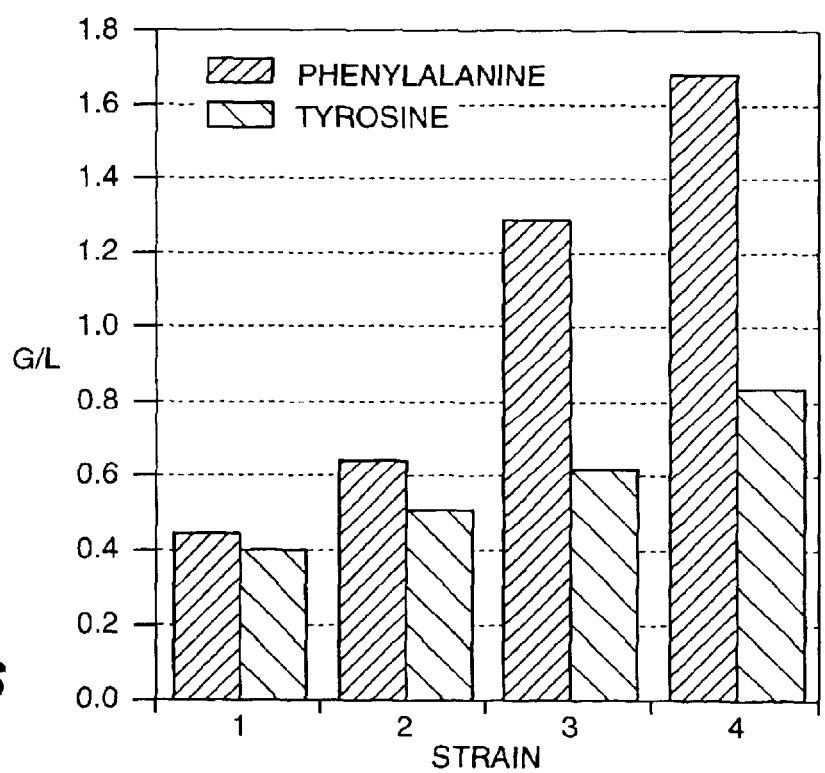
FIG._6

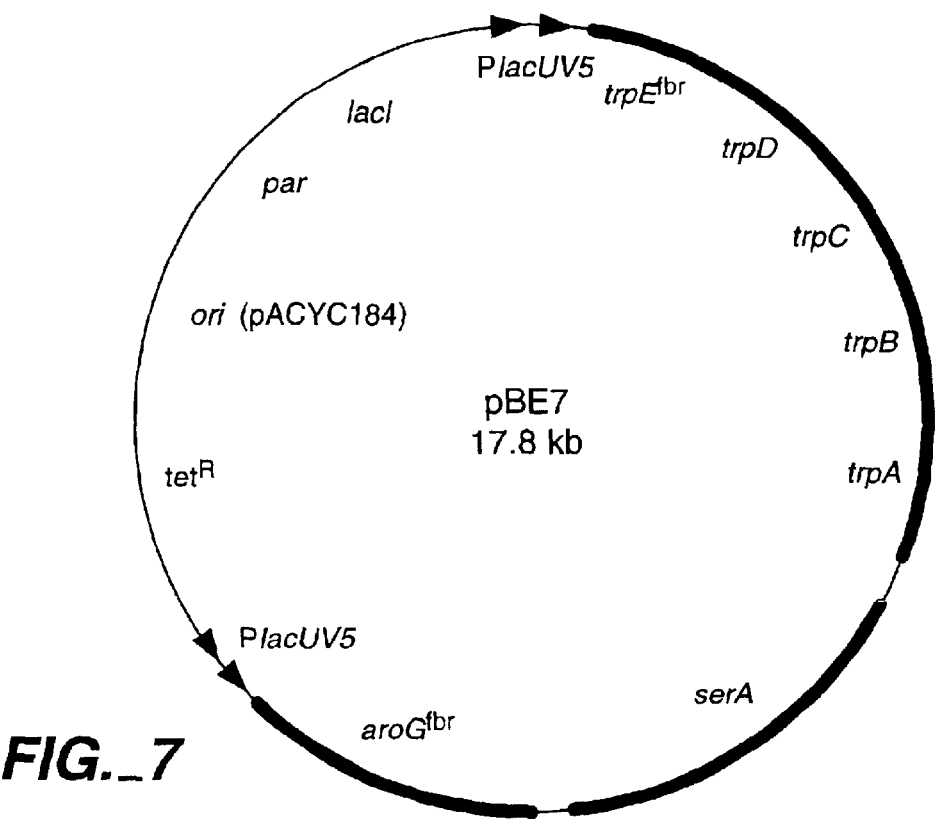
FIG._7
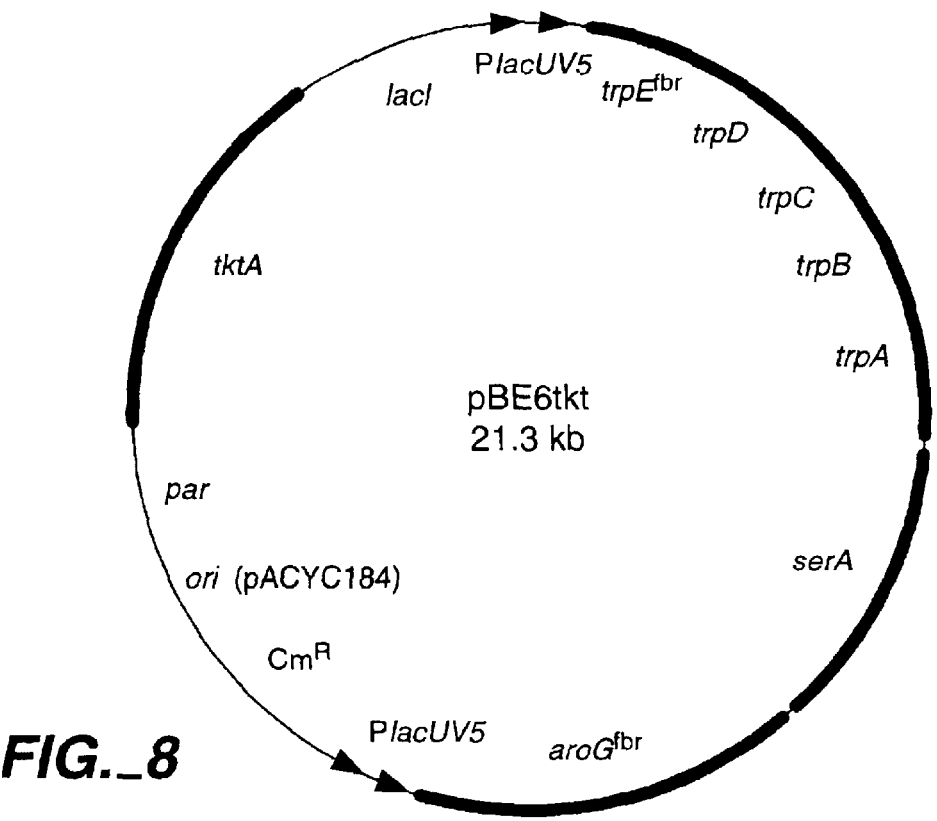
FIG._8

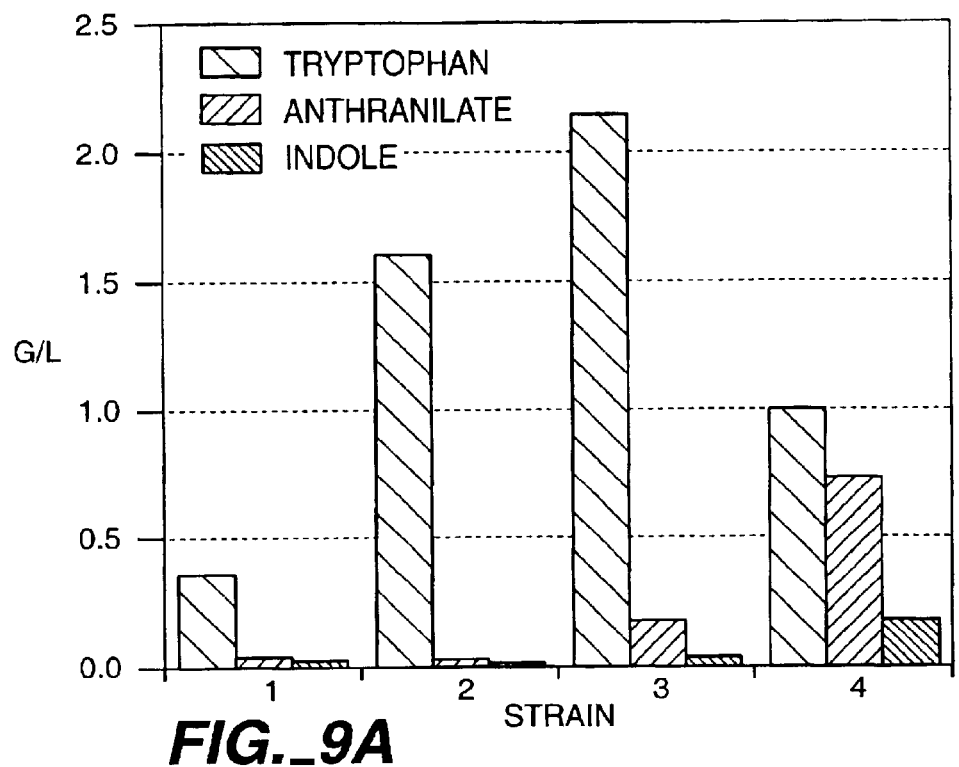
FIG._9A
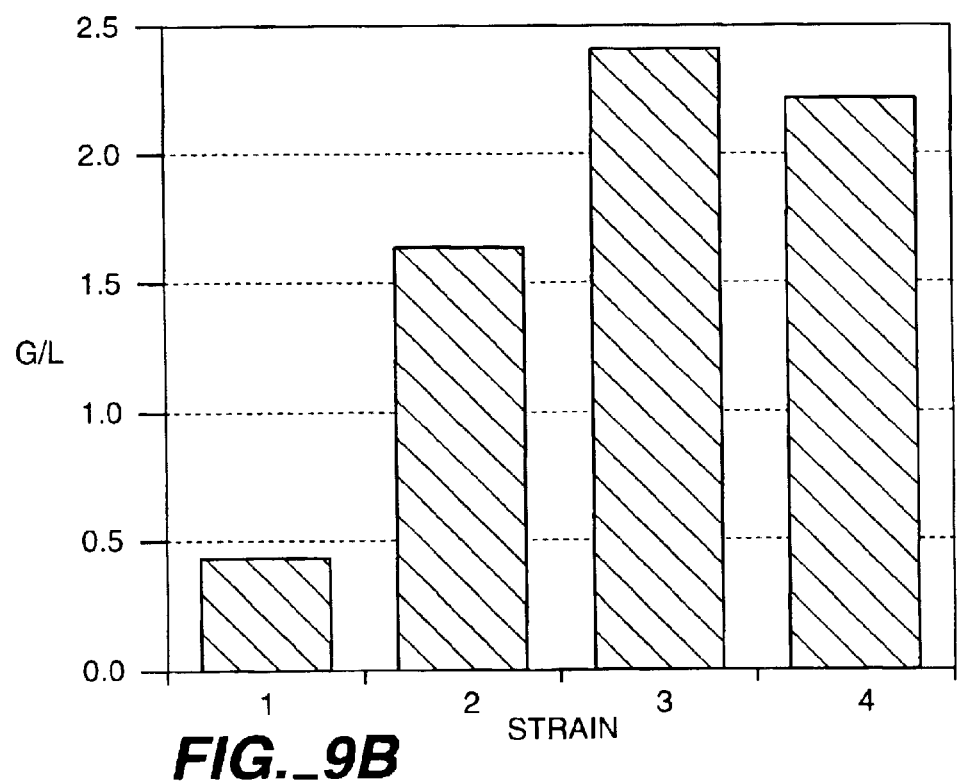
FIG._9B

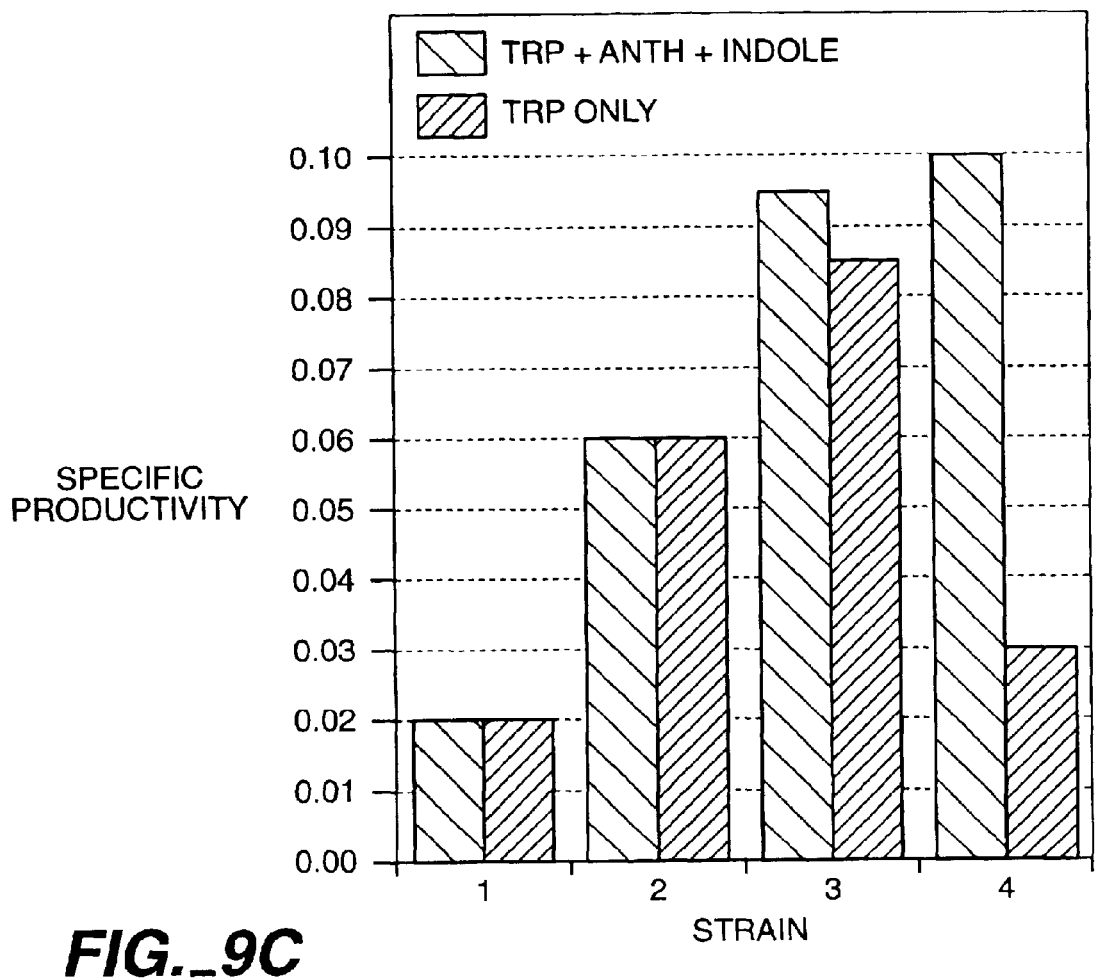
FIG._9C

APPLICATION OF GLUCOSE TRANSPORT MUTANTS FOR PRODUCTION OF AROMATIC PATHWAY COMPOUNDS

This is a continuation of application Ser. No. 08/435,510 filed May 5, 1995 now abandoned.

FIELD OF THE INVENTION

This invention relates to the enhancement of glucose transport in host strains which normally utilize the phosphoenolpyruvate:Phosphotransferase Transport System (PTS) for such transport, by reducing phosphoenolpyruvate (PEP) consumption and redirecting such PEP into a desired metabolic pathway, such as an amino acid pathway, in the host strain.

BACKGROUND OF THE INVENTION

The biosynthetic pathway known as the shikimate pathway or "common aromatic pathway" leads to the production of many aromatic compounds, including the aromatic amino acids and other compounds such as folate, melanin, indole, catechol, enterochelin, shikimate, dehydroshikimate and L-DOPA. In addition, by introducing specific cloned genes into an organism having the shikimate pathway, the range of compounds that can be produced is greatly expanded. Production of indigo via the aromatic amino acid pathway is an example of the metabolic potential of this pathway.

The cost-effective and efficient biosynthetic production of compounds or derivatives thereof along the common aromatic pathway require that carbon sources such as glucose, lactose and galactose be converted to the desired product with high percentage yield. Thus, from the standpoint of industrial biosynthetic production of aromatic compounds or other biosynthetic derivatives along the common aromatic pathway, it would be valuable to increase the influx of carbon sources into and through the common aromatic pathway, thereby enhancing the biosynthetic production of the desired compound.

Phosphoenolpyruvate (PEP) is one of the major building blocks that cells use in their biosynthetic routes, particularly in amino acid biosynthesis (see FIG. 1). For example, the synthesis of one molecule of chorismate (the common precursor to all of the aromatic amino acids) requires two molecules of PEP. To date, approaches taken to increase the influx of carbon sources into and through the common aromatic pathway typically relate to increasing the PEP supply in the cell by eliminating pyruvate kinase (pyk mutants) [1] and/or eliminating PEP carboxylase (ppc mutants) [2]. A third approach to increasing the PEP supply in the cell is to amplify the expression of the pps gene (encoding PEP synthase, which converts pyruvate to PEP) (U.S. Ser. No. 08/307,371, the disclosure of which is incorporated herein by reference). Additional approaches to increase the flux of carbon into and through the common aromatic pathway relate to increasing the intracellular supply of D-erythrose 4-phosphate (E4P), the other necessary precursor (with PEP) for aromatic biosynthesis. This approach may utilize overexpression of a transketolase gene (tktA or tktB), the product of which (transketolase) catalyzes the conversion of D-fructose 6-phosphate to E4P (U.S. Pat. No. 5,168,056, the disclosure of which is incorporated herein by reference). Another approach to increasing E4P availability may utilize overexpression of the transaldolase gene (talA) which encodes the enzyme transaldolase [3], which catalyzes the conversion of D-sedoheptulose 7-phosphate plus glyceraldehyde 3-phosphate to E4P plus fructose 6-phosphate.

Contrary to the methods previously described, the present invention addresses the issue of increasing PEP availability, and thus carbon flow into a given pathway, by generating strains capable of transporting glucose without consuming PEP during the process. Thus, the conserved PEP is then re-directed into a given metabolic pathway for the enhanced production of a desired product. These strains were generated by inactivating the PEP-dependent phosphotransferase transport system (PTS) utilized by such strains to transport glucose, and then selecting mutants that were capable of transporting glucose efficiently by a non-PTS mechanism (PEP-independent). Using the strategy of inactivating the PTS, the inventors have found that PEP is not consumed in glucose transport and, therefore, can be redirected to other metabolic pathways. These strains (Pts$^-$/glucose$^+$) have successfully been employed to increase production of tryptophan, phenylalanine, tyrosine and other compounds and are contemplated to be useful in producing other aromatic as well as non-aromatic compounds along metabolic pathways in biological systems. For example, oxaloacetate (OAA) is synthesized by at least two routes: (i) through the tricarboxylic acid (TCA) cycle; and (ii) through an anaplerotic route; the latter being catalyzed by PEP carboxylase (PPC) which converts PEP and $CO_2$ to OAA. Elimination of the PTS would increase the level of PEP available to the PPC enzyme, thus enhancing OAA production. Since OAA is the precursor of aspartate, lysine, methionine, isoleucine and threonine (see FIG. 1), production of any of the latter compounds could be enhanced in a Pts$^-$/glucose$^+$ strain.

SUMMARY OF THE INVENTION

Accordingly, there is provided by the present invention a method for increasing carbon flow into the common aromatic pathway, or any other biosynthetic or metabolic pathway that uses PEP as a precursor or intermediate, of a host cell capable of utilizing a phosphotransferase transport system for carbohydrate transport, the method comprising increasing the PEP availability to such pathway by selecting a host cell which is phenotypically Pts$^-$/glucose$^+$ and culturing the host cell with an appropriate carbon source.

In a preferred embodiment the selected host cell is modified to delete or inactivate all or substantially all of one or more of the ptsI, ptsH and crr genes encoding the EI, HPr and IIA$^{Glc}$ proteins of the PTS [6], respectively.

In another embodiment of the invention the host cell (which is phenotypically Pts$^-$/glucose$^+$) may be transformed with recombinant DNA containing genes coding for enzymes such as transketolase (tktA or tktB genes), transaldolase (talA gene) and/or phosphoenolpyruvate synthase (pps gene) such that the products therefrom are expressed at enhanced levels relative to wild-type host cells.

In another embodiment of the invention the phenotypically Pts$^-$/glucose$^+$ host may contain mutations in the pykA and/or pykF genes which encode pyruvate kinase. Likewise, the host may contain a mutation in the ppc gene, encoding PEP carboxylase. The pykA, pykF or ppc mutations would be expected to further increase availability of PEP in the cell, compared to a Pts$^-$/glucose$^+$ strain alone.

In yet another embodiment of the invention the phenotypically Pts$^-$/glucose$^+$ host cell may further comprise additional recombinant DNA containing one or more gene(s) coding for enzymes catalyzing reactions in the common aromatic pathway of the host cell. For example, the host cell may be transformed with DNA containing one or more of the aroB, aroD, aroE, aroL, aroA and aroC genes. These genes encode DHQ synthase, DHQ dehydratase, shikimate dehydrogenase, shikimate kinase, EPSP synthase and chorismate synthase, respectively (see FIG. 1). Furthermore, the host cells can be transformed with a wide variety of genes from a pathway, depending on the desired product to be made by the cells upon fermentation.

In another embodiment there is provided a method for enhancing a host cell's biosynthetic production of compounds derived from the common aromatic pathway of said host cell, the method comprising the step of culturing under suitable conditions a phenotypically Pts$^-$/glucose$^+$ host cell. The host cell may preferably be transformed with recombinant DNA containing the tktA, tktB, talA or pps genes such that the products of these genes are expressed at enhanced levels relative to wild-type host cells. Alternatively, increased levels of such gene products can be achieved by chromosomal mutation or chromosomal integration by methods available to the skilled artisan. Chromosomal mutations include mutations in the tktA, tktB, talA or pps genes themselves, or in the promoters or regulatory genes controlling their expression. In yet another embodiment of the invention relating to the overproduction of desired compounds, the host cell may further comprise additional recombinant DNA containing one or more gene(s) coding for enzymes catalyzing reactions in the common aromatic pathway of the host cell. As for tktA, tktB, talA or pps, increased expression of gene(s) encoding the enzymes of the common aromatic pathway may be effected by mutating the genes themselves, or the promoters or regulatory genes governing their expression. The host cells can be transformed with a wide variety of genes from a given pathway, depending on the desired product to be made by the cells upon fermentation.

In another aspect of the present invention there is provided a method for obtaining Pts$^-$/glucose$^+$ mutant cells, the method comprising:
 a) selecting a host cell which normally utilizes the phosphotransferase transport system;
 b) mutating the host cell by inactivating the phosphotransferase transport system;
 c) culturing the mutant host cell using glucose as a carbon source; and
 d) selecting for mutant cells which grow on glucose having a specific growth rate of at least about 0.4 h$^{-1}$.

In a preferred embodiment the host cell is modified to inactivate the phosphotransferase transport system by the deletion of one or more genes selected from ptsl, ptsH and crr, encoding the EI, HPr and IIA$^{Glc}$ proteins of the PTS, respectively.

BRIEF DESCRIPTION OF THE DRAWINGS

FIG. 1 illustrates the pathways of central carbon metabolism in *E. coli*, showing derivation of the carbon skeletons for aromatic amino acid biosynthesis. From the figure it can be seen that PTS is the major consumer of PEP. The percentages shown in the figure represent the amount of PEP channeled into the competing pathways shown, as described by Holms [4]. The bold lines in FIG. 1 indicate the steps of the tricarboxylic acid (TCA) cycle, the dashed lines indicate the glyoxylate shunt. Abbreviations: PEP, phosphoenolpyruvate; DAHP, 3-deoxy-D-arabino-heptulosonate 7-phosphate; DHQ, 3-dehydroquinate; DHS, 3-dehydroshikimate; SHK, shikimate; S3P, shikimate 3-phosphate; EPSP, 5-enolpyruvyl DAHP, 3-deoxy-D-arabino-heptulosonate 7-phosphate; DHQ, 3-dehydroquinate; DHS, 3-dehydroshikimate; SHK, shikimate; S3P, shikimate 3-phosphate; EPSP, 5-enolpyruvyl shikimate 3-phosphate; PHE, phenylalanine; TYR, tyrosine; TRP, tryptophan; EtOH, ethanol; 2-KG, 2-ketoglutarate; pgi, phosphoglucose isomerase; pyk, pyruvate kinase; pps, PEP synthase; ppc, PEP carboxylase. The aroG, aroF and aroH genes encode the three isozymes of DAHP synthase in *E. coli*. The products of the other aro genes of the common aromatic pathway were defined in the text.

FIG. 2 shows the plasmid map of pRW5. Only the relevant cloned gene and restriction site are shown. PlacUV5 represents tandem lacUV5 promoters controlling aroG expression.

FIG. 3 shows the plasmid map of pRW5tkt. Plasmid pRW5tkt was constructed by cloning a 5-kb fragment of *E. coli* DNA that contains the tktA gene [5] into the unique BamHl site of pRW5. The precise location of the tktA gene in the 5-kb fragment, or the orientation of the 5-kb fragment relative to the aroG gene, is not known.

FIG. 4 shows the enhanced production of DAH(P) in Pts strains (NF9) as compared to Pts$^+$ strains (PB103) expressing the aroG gene (plasmid pRW5) or the aroG+tkt4 genes (plasmid RW5tkt).

FIG. 5 shows the plasmid map of pCL101EA. Only the relevant cloned genes are shown. Ptac represents the tac promoter controlling expression of the aroE and the aroACB genes.

FIG. 6 shows the enhanced production of phenylalanine and tyrosine production in Pts$^-$ (NF9) and Pts$^+$ (PB103) hosts expressing the aroG gene (plasmid pRW5) or the aroG+tktA (plasmid pRW5tkt) genes, in the presence of plasmid pCL101EA (expresses the aroACBLE genes). Strain 1, PB103/pRW5, pCL101EA; Strain 2, PB103/pRW5tkt, pCL101EA; Strain3, NF9/pRW5, pCL101EA; Strain 4, NF9/pRW5tkt, pCL101EA.

FIG. 7 shows the plasmid map of pBE7. Only the relevant cloned genes are shown. PlacUV5 represents tandem lacUV5 promoters controlling expression of the aroG and trp genes.

FIG. 8 shows the plasmid map of pBE6tkt. Only the relevant cloned genes are shown. The orientation of the tktA gene relevant to the other cloned genes in plasmid pBE6tkt is not FIG. 9a shows the enhanced production of tryptophan, anthranilate and indole production in Pts$^-$ (NF9) and Pts$^{30}$ (PB103 and JB102) hosts expressing the aroG+trp genes (plasmid pBE7) in the presence or absence of plasmid pCL101EA (expresses the aroACBLE genes), or expressing the aroG+trp+tktA genes (plasmid pBE6tkt) in the presence of pCL101EA. Strain 1, PB103/pBE7; Strain 2, NF9/pBE7; Strain3, NF9/pBE7, pCL101EA; Strain 4, JB102/pBE6tkt, pCL101EA.

FIG. 9b shows the total potential tryptophan produced in Pts$^-$ (NF9) and Pts$^+$ (PB103and JB102) hosts expressing the aroG+trp genes (plasmid pBE7) in the presence or absence of plasmid pCL101EA (expresses the aroACBLE genes), or expressing the aroG+trp+tktA genes (plasmid pBE6tkt) in the presence of pCL101EA. Strain 1, PB103/pBE7; Strain 2, NF9/pBE7; Strain3, NF9/pBE7, pCL101EA; Strain 4, JB102/pBE6tkt, pCL101EA FIG. 9c shows the specific tryptophan productivity (g tryptophan/g dry cell weight/hour) in Pts$^-$ (NF9) and Pts$^+$ (PB103 and JB102) hosts expressing the aroG+trp genes (plasmid pBE7) in the presence or absence of plasmid pCL101EA (expresses the aroACBLE genes), or expressing the aroG+trp+tktA genes (plasmid pBE6tkt) in the presence of pCL101EA. Strain 1, PB103/pBE7; Strain 2, NF9/pBE7; Strain3, NF9/pBE7, pCL101EA; Strain 4, JB102/pBE6tkt, pCL101EA.

DETAILED DESCRIPTION OF THE INVENTION

One of the goals of metabolic engineering is the improvement of cellular activities by manipulation of enzymatic, transport and regulatory functions of the cell with the use of recombinant DNA techniques.

To date, most mesophilic bacteria that metabolize glucose through the glycolytic pathway have been shown to possess a PTS for glucose transport [6,7]. The PTS uses PEP to phosphorylate glucose during its internalization, providing a tight linkage between the transport of the sugar and its subsequent metabolism. Also, as PEP is twice as energetic as ATP, it can theoretically drive the uptake of its sugar substrates to a much greater extent than is allowed by the utilization of other sources of biological energy [8]. Obviously, the PTS system is advantageous in natural environments where carbon sources are scarce. However, under laboratory or industrial conditions this is not the case and, depending on the product to be biosynthesized, PEP consumption for glucose transport can decrease the availability of PEP for other biosynthetic reactions.

PEP is one of the major precursor metabolites that the cell uses in many biosynthetic reactions. Recently Varma, et al. [9] demonstrated the importance of the PEP-pyruvate node for the optimal catabolic flux distributions for maximal biochemical productions. Many biomolecules can now be produced by the fermentation of genetically modified microorganisms, for example, catechol (U.S. Pat. No. 5,272,073), indigo (U.S. Pat. No. 4,520,103 and U.S. Ser. No. 07/956,697), quinic acid (U.S. Ser. No. 07/954,623), melanin, tryptophan, phenylalanine, etc. Generally, the approach to producing these products using recombinant techniques and fermentation processes has been the amplification of the gene(s) that code for the rate-limiting enzyme (see, for example, U.S. Ser. No. 08/257,354). However, in addition to the amplification of certain genes in the pathway, another important factor to consider is the flux of carbon through the central metabolic pathways of given organisms, which is the focus of the present invention.

Host cells or strains useful in the present invention include any organism capable of utilizing a PTS system for carbohydrate transport. This includes prokaryotes belonging to the genus *Escherichia, Corynebacterium., Brevibacterium, Bacillus, Pseudomonas, Streptomyces* or *Staphylococcus*. A list of suitable organisms is provided in Table 1. The elimination of the PTS transport system in any of these organisms should potentially increase availability of PEP in the cell for alternative metabolic routes and consequently could increase production of desired compounds (e.g., aromatics) from such cells.

TABLE 1

|  | Reference |
|---|---|
| *Escherichia coli* | (6) |
| *Salmonella typhimurium* | (6) |
| *Klebsiella pneumoniae* | (6) |
| *Bacillus subtilis* | (6) |
| *Mycoplasma capricolum* | (6) |
| *Acholeplasma florum* | (10) |
| *Staphylococcus aureus* | (6) |
| *Staphylococcus carnosus* | (6) |
| *Staphylococcus xylosus* | (11) |
| *Rhodobacter capsulatus* | (6) |
| *Rhodopseudomonas sphaeroides* | (12) |
| *Streptococcus (Enterococcus) faecalis* | (6) |
| *Streptococcus mutans* | (6) |

TABLE 1-continued

|  | Reference |
|---|---|
| *Streptococcus salivarius* | (6) |
| *Streptococcus sanguis* | (6) |
| *Streptococcus sobrinus* | (13) |
| *Erwinia chrysanthemi* | (6) |
| *Xanthmonas campestris* | (6) |
| *Corynebacterium glutamicum* | (14) |
| *Brevibacterium lactofermentum* | (15) |
| *Bifidiobacterium breve* | (16) |
| *Azospirillum brasiliense* | (17) |
| *Listeria monocytogenes* | (18) |
| *Spirocheta aurantia* | (12) |
| *Lactobacillus brevis* | (12) |
| *Lactobacillus buchneri* | (12) |
| *Lactobacillus casei* | (6) |
| *Lactococcus cremoris* | (19) |
| *Lactococcus lactis* | (6) |
| *Pseudomonas aeruginosa* | (12) |
| *Vibrio alginolyticus* | (6) |
| *Vibrio furnissii* | (20) |
| *Vibrio parahaemolytica* | (12) |

Preferred strains are those known to be useful in producing aromatic compounds, including cells selected from the genera *Escherichia, Corynebacterium, Brevibacterium* and *Bacillus*. All of the bacterial strains and plasmids used in this work are listed in Tables 2a and 2b. Selection of Pts$^-$ mutants able to transport glucose efficiently can be achieved using techniques available to those skilled in the art. In the case of selecting *E. coli* Pts$^-$/glucose$^+$ mutants as exemplified herein, a chemostat was used to select glucose$^+$ mutants (from an initial population of Pts$^-$/glucose$^-$ cells) having certain specific growth rates with glucose as the sole carbon source. The spontaneous *E. coli* mutants that were selected were able to transport glucose efficiently by a non-PTS transport system. These mutants were selected by their ability to regain fast growth rates (meaning having a specific growth rate of at least about 0.4 h$^{-1}$) in the chemostat, having glucose as the sole carbon source.

The mutants characterized in this work apparently carry more than one mutation and need galactose permease (galP) activity to give the described phenotypes. It is known that the best substrate for galP is D-glucose [21]. In normal conditions (i.e., with a functional PTS) this is not of physiological relevance, especially because PTS is responsible for inducer exclusion and the galactose regulon is not induced, even if galactose is present in the medium [22]. However, the deletion of the ptsHIcrr operon creates a new situation, the preferred glucose transport system is absent and the inducer exclusion effect is lost [23]. Under these circumstances, any mutation that turns on the galP gene (or any other transporter gene which product could transport glucose) should produce cells that can utilize glucose. However, the degree of glucose utilization will depend on the specificity, level, efficiency, etc., of the transporter.

The use of a chemostat as described herein allowed the isolation of a collection of spontaneous mutants that can grow on glucose with different growth rates. Presumably these differences are due to variations on glucose transport rates.

The presently described mutants are distinguishable from those reported by Biville, et al. [24]. This was surprising since the parental strain carries the same deletion of the pts genes. Without intending to be limited to a particularly theory, it is proposed that the difference resides in the fact that in all the present experiments the level of dissolved oxygen was controlled and the cells were never under oxygen-limited conditions. The behavior of Pts⁻ strains was affected by the levels of oxygen in the medium. Again, without intending to be limited to such, a tentative hypothesis based on these mutants could be that the cells do not consume PEP during glucose transport and the intracellular levels of PEP are affected. However, considering that in *E. coli* PEP is an allosteric regulator of several enzymes like phosphofructokinase and the methylglyoxal bypass, it is difficult to believe that by altering carbon flow in the PEP-pyruvate node (i.e., by interrupting the pyruvate kinase genes and/or by using mutants that use a non-PTS transport mechanism) there will be an accumulation of PEP in the cells. It is proposed, therefore, without limitation, that in *E. coli* this situation is avoided by several mechanisms and, in order to redirect carbon flow to some other pathway(s), concomitantly to the remotion of competitive routes, the desired metabolic route(s) need be deregulated or amplified.

In an embodiment of the present invention the Pts⁻/glucose⁺ strains were further transformed with recombinant DNA coding for one or more gene(s) which direct carbon flow into and through the common aromatic pathway. One such gene is transketolase (tktA or tktB). Transketolase is a pentose phosphate pathway enzyme that catalyzes two separate reactions each of which produces E4P as a product. Amplification of the tktA gene increases intracellular concentrations of the aromatic precursor E4P (U.S. Pat. No. 5,168,056, incorporated herein by reference). Consequently, amplification of the tktA gene (i.e., increasing the intracellular E4P levels) in strains also containing elevated levels of DAHP synthase (e.g., strains having amplified expression of the aroG gene) results in a significant increase in carbon committed to the aromatic pathway compared to strains containing elevated DAHP synthase activity alone (U.S. Pat. No. 5,168,056 which is incorporated herein by reference).

Thus, having a host cell which creates a surge of carbon flow due to the amplification of transketolase in addition to a host cell which conserves PEP via inactivation of the PTS (Pts⁺), is a preferred embodiment as the effects can be additive as shown in the Examples herein. It should be noted that as the host cell is cultured in conditions which create a surge of carbon flow into the aromatic pathway, it may be necessary to identify and overcome rate-limiting steps in the pathway. This methodology is available to the artisan, see, for example, U.S. Ser. No. 08/257,354 (incorporated herein). As an example, in the following conversion

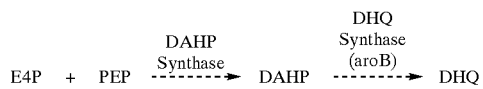

under conditions that create a surge of carbon flow into the pathway (i.e., Pts and tkt amplified strains), the activity level of DHQ synthase is insufficient to consume DAHP as fast as it is formed. As a result of this natural rate-limiting step at aroB, DAHP accumulates and is excreted into the culture supernatant. This allows DAHP accumulation to be used as a means of testing the increased intracellular PEP levels resulting from the Pts⁻/glucose⁺ mutation(s) channeled into the aromatic pathway. Similar methodologies are available with regard to PEP synthase (pps) (U.S. Ser. No. 08/307, 371) and transaldolase (talA) [3], both of which are incorporated herein.

In addition to amplification of enzymes such as transketolase to increase carbon flow into the common aromatic pathway, any genes encoding enzymes that catalyze reactions within the common aromatic pathway (for example, DAHP synthase (aroF, aroG, aroH), DHQ synthase (aroB), DHQ dehydratase (aroD), shikimate dehydrogenase (aroE), shikimate kinase (aroL, aroK, EPSP synthase (aroA) and chorismate synthase (aroC)) may be amplified in the Pts⁻/glucose⁺ mutants of the present invention. Of course, as is readily apparent to those skilled in the art, it will be desirable to amplify a variety of different genes depending on the desired product. For example, if the desired product is tryptophan, any of the genes in the tryptophan-specific segment of the aromatic pathway may be amplified, including the genes coding for the enzymes tryptophan synthase (trpA and trpB), phosphoribosyl anthranilate isomerase-indoleglycerol phosphate synthase (trpC), anthranilate phosphoribosyl transferase (trpD) and anthranilate synthase (trpE), while other genes may be deleted, such as tryptophanase (tnaA).

If, for example, the desired compound is catechol, one may, in addition to utilizing a Pts⁻/glucose⁺ mutant, further transform this mutant with DNA encoding one or more of the following enzyme(s): DAHP synthase (aroF, aroG, aroH); 3-dehydroquinate (DHQ) synthase (aroB); transketolase (tktA or tktB); 3-dehydroshikimate (DHS) dehydratase (aroZ) or protocatechuate (PCA) decarboxylase (aroY) (see U.S. Ser. No. 08/122,919 and U.S. Pat. No. 5,272,073, the disclosure of such being incorporated herein by reference). Furthermore, by way of example, if the desired product is adipic acid, one or more of the following enzyme(s) may be overexpressed (by amplification of the corresponding gene): 3-dehydroshikimate (DHS) dehydratase (aroZ); protocatechuate (PCA) decarboxylase (aroY) or catechol 1,2-dioxygenase (catA); and, optionally, transketolase (tktA or tktB); DAHP synthase (aroF, aroG, aroH) or DHQ synthase (aroB). (See U.S. Ser. No. 08/122,920, the disclosure of any patent issuing thereon being incorporated herein by reference.)

Likewise, if the desired product is indigo, the Pts⁻/glucose⁺ host strain may be further transformed with DNA encoding a polypeptide analog of a tryptophan synthase beta-submit and DNA encoding an aromatic dioxygenase enzyme. (See U.S. Ser. No. 07/956,697, the disclosure of any patent issuing thereon being incorporated herein by reference.)

Further examples of amplification of various genes (depending on the desired compound) in a Pts⁻ mutant strain are provided in the Examples that follow.

Thus, having provided a Pts⁻/glucose⁺ host strain which conserves PEP and thus increases the carbon flux into the pathway (by redirecting the PEP into the desired pathway), the inventors have provided a host system which can be utilized for the production of virtually any compound or derivative along the common aromatic pathway, as well as other pathways such as the non-aromatic pathways to lysine and threonine, etc.

Saier, et al. [25] have reported that a strain of *Salmonella typhimurium* deleted of some phosphotransferase genes (such that they do not grow on minimal medium plus glucose) gave rise to mutants that can use glucose as the only carbon source. These mutants were found to have a mutation in the galR gene, and thus had a constitutively expressed galactose permease gene (galP) which resulted in glucose transport.

In order to obtain *E. coli* Pts⁻ mutants that could utilize glucose efficiently, strains PB11 and NF6 which carry a deletion of the ptsH, ptsI and crr genes (the ptsHlcrr operon) were used in the present experiments. The introduction of the pts deletion was performed by methods detailed in the Experimental Procedures section below.

Generally, the methodology employed was as follows. PB11 and NF6 are derivatives of JM101 [30] or PB103 (Trp+ derivative of C534 [33]) strains, respectively, in which the ptsHIcrr operon has been deleted. Although this deletion can be accomplished using many different methodologies, in the present invention we utilized generalized transduction as described by Silhavy, et al. [26], using P1 vir phage to perform the transduction and strain TP2811 [27] as the donor of the ptsHIcrr deletion. This process was carried out in two stages. First, a cell-free suspension of phage was prepared by growing bacteriophage P1 vir on strain TP2811. In the TP2811 strain most of the ptsHIcrroperon has been deleted and the kanamycin-resistant marker was inserted in the same DNA region [27]. The obtained P1 vir lysate is able to transduce the ptsHIcrr deletion and kanamycin resistance marker simultaneously. Secondly, these phage were used to infect a genetically different recipient strain (JM101 or PB103) and genetic recombinants (transductants) were selected by plating the infected cells on MacConkey-glucose plates containing kanamycin. After incubating the plates for 16 hours at 37° C., several white colonies appeared. It is important to note that the recipient strains (JM101 and PB103) are kanamycin sensitive and form red colonies on MacConkey-glucose plates. The color of the colony is an important factor to consider in this experiment. The MacConkey-glucose plates contain an indicator dye that, depending on the pH, can vary from white to deep red. If the cells can transport glucose at a fast rate, normally they will secrete organic acids and produce red colonies. On the other hand, if glucose transport is diminished or absent, the cells will not produce organic acids and the colonies will be white.

The fact that after the transduction all the resulting kanamycin-resistant colonies were white indicated that the ability of the cells to assimilate glucose was affected, probably due to the transfer of the ptsHIcrr operon deletion. To corroborate this assumption we selected some transductants and inoculated them in minimal medium containing glucose as the only carbon source. As expected, after 12 hours of incubating the cultures at 37° C., no cell growth was detected. Under the same conditions, strains JM101 and PB103 grew very well (data not shown). Another test for the absence of the PTS system is based on the fact that Pts- strains become resistant to the antibiotic fosfomycin [28]. This phenotype was also tested in our transductants and it was found that they were resistant to such antibiotic (data not shown).

Based on these results, it is concluded that we transferred the deletion of the ptsHIcrr operon to the recipient strains (JM101or PB103). The Pts- derivative of JM101 was designated PB11, while the Pts- derivative of PB103 was designated NF6.

The ptsHIcrr deletion causes a very pleiotropic phenotype, affecting the utilization of PTS and non-PTS carbohydrates. Furthermore, it affects the assimilation of tricarboxylic acid intermediates and certain amino acids [23]. Biville, et al. [24] demonstrated that an E. coli strain carrying the same deletion was able to grow very slowly on glucose as the only carbon source. After 2–3 days of incubation, this strain gave rise to fast growing cells. It was found that these mutants were able to produce pyrroloquinoline quinone (PQQ) and have glucose dehydrogenase activity. Presumably this strain assimilated glucose by the Entner-Duodoroff pathway, by converting glucose into gluconate [24].

In order to select spontaneous glucose+ revertants of the Pts- strain (PB11), selection was performed with a chemostat [29]. The experiment was designed to isolate mutants with a specific growth rate of at least 50% of the parental (Pts+) strain (JM101) (see Experimental Procedures section below). By increasing the feed flow rate in the chemostat, mutants were selected with different specific growth rates. These growth rates were confirmed in independent experiments for each strain.

With this procedure for selecting for glucose+ mutants of PB11 having a specific growth rate of at least $0.4\ h^{-1}$, a collection of mutants was obtained. Initially 8 colonies were purified to single colonies by re-streaking several times on MacConkey-glucose agar plates. Some of these isolates presented a normal E. coli colony morphology with a homogeneous red color. Others, however, presented an unstable phenotype. Still others were mucoid or produced small colonies. Differences in the degree of red color of the colony were also observed. One of the stable, non-mucoid isolates (designated PB12) that had a normal colony morphology and homogeneous red color was further characterized (see below).

After increasing the feed flow rate to the chemostat to select for Pts-/glucose+ mutants having a specific growth rate of $0.8\ h^{-1}$, the cells were again plated out of the chemostat. All of the colonies obtained now had the normal, stable E. coli colony morphology, were non-mucoid and had a homogeneous red color. One such mutant, designated PB13, was further characterized as described below.

In addition to the Pts-/glucose+ mutants (PB12 having a specific growth rate of $0.4\ h^{-1}$, and PB13 having a specific growth rate of $0.8\ h^{-1}$) derived from the E. coli JM101 host, another Pts-/glucose+ mutant designated NF9 was derived the same way but from E. coli strain PB103. NF9, like mutant PB13, had a specific growth rate in the chemostat of $0.8\ h^-$, and had the normal E coil colony morphology described above for PB13. Some of the phenotypic characterization described below for mutants PB12 and PB13 was also carried out for mutant NF9. Mutants PB13 and NF9 gave similar results in these tests (data not shown).

Strains JM101 (parent), PB11 (Pts-), PB12 (Pts-/glucose+, specific growth rate $0.4\ h^{-1}$) and PB13 (Pts-/glucose+, specific growth rate $0.8\ h^{-1}$) were compared for ability to oxidize a variety of carbon sources using the Biolog microplate assay system as described in the Experimental Procedures section below. The ability or inability of the strains to oxidize a carbon source was found to be very reproducible. It should be noted that oxidation of a particular carbon source does not always indicate that the test organism can utilize that carbon source for growth.

The introduction of the pts deletion in the JM101 strain had a strong affect on the ability of the cells to oxidize several carbon sources (PB11 strain) (Table 3). However, after selecting mutants that could grow on glucose with different growth rates (strains PB12 and PB13), some of the phenotypes changed and some remained the same. In general, the reversion to a glucose+ phenotype did not produce a new phenotype not present in the parental (Pts+) strain JM101. Also, the two Pts-/glucose+ strains analyzed presented a very similar carbon usage pattern.

Based on previous information in the literature, [24, 25], it was thought that the Pts-/glucose+ mutants selected in this work were using a constitutive galactose permease to transport glucose. To confirm this notion the galP gene in strains PB11, PB12 and PB13 was interrupted with a Tn10 transposon. This was accomplished by using a P1 vir phage lysate prepared on E. coli strain CGSC6902 (see Table 2a) to transduce the galP::Tn10 insertion to strains PB11, PB12 and PB13, creating strains PB11P, PB12P and PB13P, respectively. The strains where galP was interrupted lost their ability to utilize glucose as a carbon source (judged by their color on MacConkey-glucose plates). These results indicate that the Pts$^-$/glucose$^+$ mutants need the galactose permease to produce the glucose$^+$ phenotype. Saier, et al. [25] reported that in a Pts$^-$ background the introduction of the galR mutation is sufficient to produce a glucose$^+$ phenotype. More recently it has been shown that in E. coli there are two repressors, galR and galS, involved in the control of the galactose regulon [22]. Based on this, PB11 derivatives carrying the galR, galS or galR galS mutations were constructed by P1 vir transduction using the galS::Tn10 strain AG701 and/or the galR::Cm$^R$ strain JT247 as the source of the inactivated galS and galR genes. The resulting strains were designated PB111 (Pts$^-$/glucose$^+$, galR::Cm$^R$), PB114 (Pts$^-$/glucose$^+$, galS::Tn10) and PB115 (Pts$^-$/glucose$^+$, galR::Cm$^R$, galS::Tn10). After plating these mutants on MacConkey-glucose plates, the color of the colonies was scored after 24 h. None of the mutations were enough to give a red phenotype on MacConkey-glucose plates. However, the introduction of the galR mutation into the PB11 strain did produce pink colonies, suggesting that this mutation partially restored the ability of the cells to utilize glucose.

Thus, it is believed that the Pts$^-$/glucose$^+$ mutants isolated in this work carry more than one mutation. This belief is supported by the fact that using P1 vir phage lysates prepared from strains PB12 and PB13, we were unable to transduce strain PB11 back to the ability to grow in M9-glucose medium. These experiments were repeated several times, using different amounts of phage. Furthermore, the ability of those phage lysates to transduce an unrelated genetic marker was verified in the same set of experiments (data not shown).

The fact that the Pts$^-$/glucose$^+$ mutants of the present invention need galP for growth on glucose distinguishes them from the mutants reported by Biville [24] that were able to sustain high growth rates on glucose in the absence of a functional galP gene. Furthermore, the present mutants do not produce gluconate and utilize glucose in MacConkey-glucose plates under anaerobic conditions (data not shown), while the mutants isolated by Biville [24] were oxygen dependent for the oxidation of glucose into gluconate.

Experimental Procedures

Bacterial Strains and Growth Conditions

Bacterial strains are listed in Table 2a, while the plasmids used are listed in Table 2b. Pts$^-$ strains PB11 and NF6 were obtained by P1 vir phage transduction using TP2811 [27] as donor as described by Silhavy [26]. Several of the phenotypic characteristics of the Pts$^-$ mutation were confirmed using MacConkey-agar-base plates supplemented with different carbohydrates. Also, the resistance to the antibiotic fosfomycin was used as another indicator of the pts$^-$ phenotype [28]. M9 minimal medium supplemented with thiamine and glucose [32] was used for determination of growth characteristics in liquid medium.

Utilization of Different Carbon Sources

To characterize the catabolic properties of the strains, ES and GP Microplates (Biolog, Inc.) were utilized. Equal numbers of cells were inoculated into the 96-well microplate, incubated 24 hours at 37° C. and the results were analyzed with a microplate reader and computer software of the supplier (Biolog, Inc.).

TABLE 2a

| Strains | Relevant Genotype and Characteristics | Source or Reference |
|---|---|---|
| JM101 | supE, thi, (Δlac-proAB) F', [traD36, lacI$^q$, lacZΔ M15, proAB] | [30] |
| TP2811 | F', xyl, argH1, lacX74, aroB, ilvA Δ(ptsH, ptsI, crr), Km$^R$ | [27] |
| CGSC6902 | F', his, leu, ilvA, Δlac, mglP, galP::Tn10 | E. coli Genetic Stock Center |
| AG701 | galS::Tn10 | [31] |
| JT247 | galR::Cm$^R$ | [31] |
| PB11 | JM101, Δ(ptsH, ptsI, crr), Km$^R$ | [This Work] |
| PB12 | same as PB11, but glucose$^+$ with a specific growth rate of 0.4h$^{-1}$ | [This Work] |
| PB13 | same as PB11, but glucose$^+$ with a specific growth rate of 0.8h$^{-1}$ | [This Work] |
| PB11P | same as PB11, but galP::Tn10 | [This Work] |
| PB12P | same as PB12, but galP::Tn10 | [This Work] |
| PB13P | same as PB13, but galP::Tn10 | [This Work] |
| PB111 | same as PB11, but galR::Cm$^R$ | [This Work] |
| PB114 | same as PB11, but galS::Tn10 | [This Work] |
| PB115 | same as PB11, but galR::Cm$^R$, galS::Tn10 | [This Work] |
| PB103 | F' ΔlacU169 trpR tnaA2 anthranilate$^R$ (Trp$^+$ derivative of strain C534 [33]) | [This Work] |
| JB102 | same as PB103, but serA | [This Work] |
| NF6 | same as PB103, but Δ(ptsH, ptsI, crr), Km$^R$ | [This Work] |
| NF9 | same as NF6, but glucose$^+$ with a specific growth rate of 0.8h$^{-1}$ | [This Work] |
| NF6P | same as NF6, but galP::Tn10 | [This Work] |
| NF9P | same as NF9, but galP::Tn10 | [This Work] |

TABLE 2b

| Plasmids | Relevant Cloned Gene(s) | Source or Reference |
|---|---|---|
| pRW5 | P$_{lacUV5}$-aroG$^{fbr}$ | [This Work] |
| pRW5tkt | same as pRW5, but also containing tktA | [This Work] |
| pCL101EA | P$_{tac}$-aroACB, aroL, P$_{tac}$-aroE | [This Work] |
| pBE7 | P$_{lacUV5}$-aroG$^{fbr}$, P$_{lacUV5}$-trpE$^{fbr}$ DCBA, serA | [This Work] |
| pBE6tkt | P$_{lacUV5}$-aroG$^{fbr}$, P$_{lacUV5}$-trpE$^{fbr}$ DCBA, serA, tktA | [This Work] |

EXAMPLE 1

Transduction of the ptsHIcrr Operon Deletion to the JM101 and PB103 Strains

Phase 1: Preparation of P1 vir Phage Lysate

To prepare a P1 vir phage lysate from strain TP2811 [27], 0.5 ml of a overnight culture of this strain were inoculated in 5 ml of LB culture media (1% of Bacto-tryptone, 0.5% of Bacto-yeast extract, 1 % of sodium chloride, pH 7.4) containing 0.2% glucose and 5 mM CaCl$_2$. The culture was incubated for 30 min at 37° C. with aeration. A 0.1 ml volume of a P1 vir lysate (approx. 5×10$^8$ phage/ml) was added and the mixture was shaken at 37° C. for 2–3 hr until the cells lysed. 0.1 ml of chloroform were added and the mixture vortexed. The resulting sample was centrifuged at 4500 g for 10 min to pellet the debris. The supernatant was transferred to a sterile tube. 0.1 ml of chloroform were added to the tube, mixed and stored at 4° C.

Phase 2: Genetic Transduction

To perform the transduction, a single colony of the recipient strain (JM101 or PB103, see Table 2a) was inoculated in 5 ml of LB culture media and incubated with shaking at 37° C. overnight. The overnight culture was centrifuged at 1500 g for 10 min and the cell pellet resuspended in 2.5 ml of 10 mM $MgSO_4$ containing 5 mM $CaCl_2$. In a sterile tube, 0.1 ml of this cell suspension and 0.1 ml of the phage lysate were combined and incubated for 30 min at 30° C. without shaking. Controls lacking phage were also included.

0.1 ml of 1 M sodium citrate was added to the tubes and mixed. 1 ml of LB medium was then added and the mix was incubated at 37° C. for 1 hr and plated on MacConkey-agar base media containing 50 micrograms/ml of kanamycin and 1% glucose.

Several white colonies appeared on the plates after 12 hrs of incubation. These colonies were purified further by plating on fresh plates containing MacConkey-agar base media, 50 micrograms/ml of kanamycin and 1% glucose. These white colonies, as indicated above, were unable to transport glucose, and thus were believed to comprise the deletion of the ptsH/crr operon. One of the purified white colonies derived from each of the parental strains (JM101 or PB103) was selected for further work. These Pts⁻/glucose⁺ mutants were designated PB11 (derived from JM101) and NF6 (derived from PB103) (see Table 2a).

EXAMPLE 2

Method of Making the Selection in a Chemostat

Strain PB11 or strain NF6 was inoculated in a 1 liter chemostat containing M9 medium supplemented with 0.2% glucose and incubated at 37° C. The dissolved oxygen was maintained above 20% by controlling the impeller speed. The pH of the medium was maintained at 7.0 by base addition. After the culture reached on $OD_{600}$ of approximately 2.5, the washing of the fermenter was initiated by feeding fresh M9 medium at a 0.52 liters/hour rate. This flow rate should wash out all the cells growing with a specific growth rate less than 0.4 $h^{-1}$ (under the same conditions the specific growth rate of the Pts⁺ parental strain was 0.8 $h^{-1}$). After at least 3 residence times, the feed flow rate was increased to wash out cells with a growth rate less than 0.5 $h^{-1}$. This procedure was repeated (i.e., 0.1 increments) until strains were selected with a doubling time of at least 0.8 $h^{-1}$. No attempts were made to isolate strains with a faster growth rate. Before each incremental increase in glucose feed flow rate, samples were taken from the chemostat, diluted and plated on MacConkey-glucose plates. After incubating the plates 24 hrs at 37° C., plates were scored for total colony number, total red colonies, colony morphology, etc., as a means of tracking the appearance of Pts⁻/glucose⁺ cells having a normal E. coli colony morphology and a homogeneous red color. As stated above, only strains having a normal, non-mucoid colony morphology and a homogeneous red color were studied further. All of the Pts⁻/glucose⁺ mutants isolated from the chemostat that were further characterized are listed in Table 2a. PB12 and PB13 were derived from strain PB11, while NF9 was derived from strain NF6.

EXAMPLE 3

Phenotypic Characterization of Pts⁻/glucose⁺ Mutants

To characterize the catabolic properties of the JM101, PB11, PB12 and PB13 strains (see Table 2a), ES and GP microplates were used as outlined in the Experimental Procedures section. After performing several experiments with this system we found that the quantitative values varied. However, the ability or inability to oxidize a carbon source was very reproducible. The data shown in Table 3 provide the qualitative results of this experiment. These data reflect the ability (+) or inability (−) of a given strain to oxidize a certain carbon source. The pleiotropic nature of the ptsHIcrr deletion is evident from these results.

TABLE 3

| Carbon Source | Strain JM101 | Strain PB11 | Strain PB12 | Strain PB13 |
| --- | --- | --- | --- | --- |
| Glucose | + | − | + | + |
| L-Asn | + | − | − | − |
| L-Gln | + | − | − | +/− |
| L-Pro | + | − | − | − |
| L-Asp | + | − | − | − |
| L-Glu | + | − | − | − |
| L-Thr | + | − | − | − |
| D-Ala | + | − | − | + |
| Glycyl-L-Asp | + | +/− | + | + |
| Glycyl-L-Glu | + | +/− | + | + |
| N-Acetyl-D-Glucosamine | + | − | − | − |
| D-Galactonic acid γ-Lactone | − | − | + | + |
| Glycerol | + | + | + | + |
| Saccharic acid | + | − | − | − |
| D-Glucoronic | + | + | + | + |
| D-Malic acid | + | − | +/− | + |
| Fumaric acid | + | − | − | − |
| D-Sorbitol | + | − | − | − |
| Lactose | − | − | − | − |
| Fructose | + | − | − | − |
| D-Mannose | + | − | − | − |
| D-Galactose | + | + | + | + |
| L-Rhamnose | + | − | + | + |
| D-Gluconic acid | + | + | + | + |
| α-Methyl Galactoside | + | − | + | + |
| L-Galactonic acid γ-Lactone | + | − | + | + |
| Mucic acid | + | − | + | + |

EXAMPLE 4

Interruption of galP

To determine if glucose transport in the Pts⁻/glucose⁺ strains occurs via the galactose permease (encoded by the galP gene), the galP gene was interrupted in the JM101, PB11, PB12, PB13, PB103 and NF9 strains (see Table 2a). Example 1 was repeated with the following modifications: To prepare the P1 vir phage lysate, strain CGSC6902 (Table 2a) was used as donor of the galP::Tn10 mutation. After performing the genetic transduction, using strains JM101, PB103, PB11 (Example 1), NF6 (Example 1), PB12 (Example 2), PB13 (Example 2) or NF9 (Example 2) as recipients, the cells were plated on MacConkey-agar base medium containing 50 micrograms/ml of kanamycin, 10 micrograms/ml of tetracycline and 1% glucose. After 12 hours of incubation at 37° C., the phenotypes were scored. Results are shown in Table 4. After transferring the galP::Tn10 insertion to all of the Pts⁻/glucose⁺ strains selected in this invention as per Examples 1 and 2, they had a white phenotype. This strongly supports the hypothesis that glucose transport in the Pts⁻/glucose⁺ strains is occurring via the galactose permease (encoded by galP).

TABLE 4

| Strain | Phenotype |
| --- | --- |
| JM101 | Red |
| PB11 | White |
| PB12 | Red |
| PB13 | Red |
| PB11P (galP⁻) | White |
| PB12P (galP⁻) | White |
| PB13P (galP⁻) | White |

TABLE 4-continued

| Strain | Phenotype |
|---|---|
| PB103 | Red |
| NF6 | White |
| NF9 | Red |
| NF6P (galP⁻) | White |
| NF9P (galP⁻) | White |

EXAMPLE 5

Effect of the galR::Cm$^R$, galS::Tn10 Mutations

The results presented in Example 4 strongly suggested that in the Pts⁻/glucose⁺ strain, glucose transport occurs via the galactose permease, encoded by galP. The galR and galS genes encode the repressor and is repressor, respectively of the gal operon [31], and galR is known to repress expression of the galP gene [25]. Thus, inactivation of the galR (and possibly the galS) gene in the Pts⁻ background should lead to derepression of the galactose permease and a glucose⁺ phenotype. This hypothesis was tested as follows.

To transfer the galR::Cm$^R$ and/or the galS::Tn10 mutations to the PB11 strain, Example 1 was repeated with the following modifications: To prepare the P1 vir phage lysate, strains AG701 (galS::Tn10, Table 2a) or JT247 (galR::Cm$^R$, Table 2a) were used as donors. The lysates prepared on these strains were used to transduce the Pts⁻/glucose⁺ strain PB11, selecting for transductants having the appropriate antibiotic resistance. Three derivative strains were obtained: PB111 (galR::Cm$^R$); PB114 (galS::Tn10) and PB115 (galR::Cm$^R$, galS::Tn10). These strains, along with the parental strains JM101 and PB11, were analyzed for their ability to utilize glucose by streaking on MacConkey-agar containing 1% glucose. The results shown in Table 5 indicate that none of the mutation(s) introduced were sufficient to completely restore glucose utilization (i.e., produce red colonies). However, the introduction of galR::Cm$^R$ mutation to the PB11 strain (strains PB111 and PB115) generated pink colonies, indicating that the ability to transport glucose and secrete organic acids had been partially restored.

TABLE 5

| Strain | Phenotype |
|---|---|
| JM101 | Red |
| PB11 | White |
| PB111 | Pink |
| PB114 | White |
| PB115 | Pink |

The results presented in Examples 1–5 show that the PTS can be effectively abolished by deletion of the ptsHIcrr operon, resulting in cells that are unable to utilize glucose (glucose⁺) (Example 1). Spontaneous glucose⁺ mutants of these strains can be obtained using the present novel method of selecting glucose⁺ derivatives in a chemostat (Example 2). The pleiotropic effect of the ptsHIcrr deletion is evident from the large number of phenotypic differences between the Pts⁺ (parental) strain and the Pts⁻ or Pts⁻/glucose⁺ derivatives (Example 3). Inactivation of the galP gene, encoding galactose permease, in the Pts⁻/glucose⁺ mutants abolishes their ability to utilize glucose, strongly suggesting that the Pts⁻/glucose⁺ strains use the galactose permease for glucose transport (Example 4). Further support for this hypothesis comes from the fact that inactivation of the galR repressor, which represses expression of galP, in a Pts⁻/glucose⁺ background, partially restores the ability of the strain to utilize glucose (Example 5).

The three remaining examples that follow (Examples 6, 7 and 8) relate specifically to directing the increased PEP afforded by the Pts⁻/glucose⁺ mutation(s) into a specific biosynthetic pathway, in this case the aromatic amino acid pathway, although the present invention is not limited to this pathway alone.

EXAMPLE 6

The method described above for selection of Pts⁻/glucose⁺ mutants that import glucose via a non-PEP-dependent mechanism should result in increased intracellular availability of phosphoenolpyruvate (PEP). One approach to testing this hypothesis is to compare carbon commitment to the aromatic amino acid biosynthetic pathway (a pathway in which PEP is an initial precursor) in the Pts/glucose+mutants and their respective parental (Pts⁺) strains. The PEP that is spared during glucose transport in Pts⁻/glucose⁺ mutants should be available for direction into the aromatic pathway. To test whether Pts⁻/glucose⁺ strains direct more PEP to aromatic biosynthesis, strain PB103 (a Trp⁺ derivative of strain C534 [33]) and its Pts⁻/glucose⁺ derivative NF9 were used (refer to Table 2a for strain descriptions). In minimal-glucose medium, the Pts⁻/glucose⁺ mutant NF9 exhibits a growth rate identical to it's parent strain PB103 (data not shown).

To measure carbon commitment to the aromatic pathway, strains PB103 and NF9 were each transformed with plasmids designated pRW5 and pRW5tkt (FIGS. 2 and 3). Plasmid pRW5 contains the *E. coil* aroG gene cloned under control of tandem lacUV5 promoters [34]. Thus, the level of expression of aroG is controlled by addition to the bacterial cultures of the inducer isopropyl γ-D-thiogalactopyranoside (IPTG). The aroG gene encodes the enzyme DAHP synthase, which catalyzes the initial reaction of the aromatic amino acid pathway (refer to the legend to FIG. 1 for abbreviations):

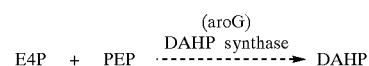

Strains containing pRW5, when grown in medium containing IPTG, have amplified DAHP synthase activity (unpublished). This elevated DAHP synthase activity serves to pull E4P and PEP away from central metabolism and direct them into the aromatic amino acid pathway (FIG. 1). Indeed, elevated levels of DAHP synthase are prerequisite to production of compounds derived from the aromatic pathway.

Plasmid pRW5tkt is identical to pRW5 but also contains the cloned *E. coli* tktA gene, encoding the enzyme transketolase (U.S. Pat. No. 5,168,056). Transketolase is a pentose phosphate pathway enzyme that catalyzes two separate reactions each of which produces E4P as a product. Thus, amplification of a tkt gene (tktA or tktB) increases intracellular concentrations of the aromatic pathway precursor E4P. Consequently, amplification of a tkt gene (i.e., increasing the intracellular E4P level) in strains also containing elevated levels of DAHP synthase (e.g., strains containing amplified aroG) results in a significant increase in carbon committed to the aromatic pathway compared to strains containing elevated DAHP synthase activity alone.

The second enzymatic step of the aromatic amino acid pathway is catalyzed by the enzyme dehydroquinate (DHQ)

synthase. This enzyme, encoded by the aroB gene, catalyzes the conversion of DAHP to DHQ.

Under conditions that create a surge of carbon flow into the aromatic pathway, e.g., in strains containing pRW5 or pRW5tkt, the activity level of DHQ synthase is insufficient to consume DAHP as fast as it is formed. As a result of this natural rate-limiting step at aroB, DAHP accumulates and is excreted into the culture supernatant. This allows DAHP accumulation be used as a means of testing the hypothesis that the increased intracellular PEP levels resulting from the Pts⁻/glucose⁺ mutations can be channeled into the aromatic amino acid pathway.

Four strains were compared for DAHP production:

| Strain | Pts Phenotype | Cloned Gene(s) on Plasmid |
| --- | --- | --- |
| PB103/pRW5 | Pts⁺ | aroG |
| PB103/pRW5tkt | Pts⁺ | aroG + tktA |
| NF9/pRW5 | Pts⁻/glucose⁺ | aroG |
| NF9/pRW5tkt | Pts⁻/glucose⁺ | aroG + tktA |

The strains were grown with shaking in 30 ml flask cultures at 37° C. The medium used was YE medium, which contains (per liter of distilled water): 15 g yeast extract, 14 g $K_2HPO_4$, 16 g $KH_2PO_4$, 5 g $(NH_4)_2SO_4$, 15 g glucose, 1 g $MgSO_4$.7 H2O and 1 drop of P-2000 antifoam. Cultures were inoculated with cells from overnight seed cultures. The initial $OD_{660}$ of the cultures was 0.2. IPTG was added to the cultures (to induce high level expression of the aroG gene on plasmids pRW5 or pRW5tkt) when the $OD_{660}$ reached 2.0. The pH of the cultures was maintained at 6.5 throughout the experiment by periodic additions of 45% KOH. Samples of the cultures were withdrawn at specified intervals, the cells removed by centrifugation, and the supernatant (cell-free culture broth) was assayed for DAHP using the standard thiobarbituric acid assay [35].

The results shown in FIG. 4 show that the Pts⁻/glucose⁺ strain NF9 containing plasmid pRW5 accumulates over 2× more DAHP than the isogenic control strain PB103/pRW5. This level of increase in DAHP production is similar to that observed for the Pts⁺ strain PB103/pRW5tkt, which contains amplified aroG+tktA. The highest level of DAHP production was observed in the Pts⁻/glucose⁺ strain NF9 containing pRW5tkt (about 2× DAHP over PB103/pRW5tkt or NF9/pRW5, and about 4× DAHP over PB103/pRW5).

These results show that in the Pts⁻/glucose⁺ strains the carbon commitment to the aromatic amino acid pathway is doubled compared to the isogenic control strain. Furthermore, the individual positive effects of the Pts⁻/glucose⁺ mutations and amplified tktA act in an additive fashion, resulting in a 4-fold increase in carbon commitment to the aromatic amino acid pathway relative to the control strain.

EXAMPLE 7

In Example 6, it was shown that carbon commitment to the aromatic amino acid pathway is doubled in the Pts⁻/glucose⁺ strains NF9/pRW5 and NF9/pRW5tkt relative to their isogenic control (Pts⁺) strains, PB103/pRW5 and PB103/pRW5tkt, respectively. To illustrate this phenomenon further, each of the above-mentioned strains was transformed with plasmid pCL101EA (FIG. 5). The latter plasmid is compatible with the pRW5 and pRW5tkt plasmids and contains the cloned E. coli aroA, aroC, aroB, aroL and aroE genes (referred to collectively as aroACBLE). The presence of pCL101EA results in elevated levels of the aroACBLE gene products, which catalyze five of the six steps within the common trunk of the aromatic amino acid pathway leading up to the branch point intermediate chorismate (depicted schematically below). Abbreviations used in the diagram are as given in the legend to FIG. 1.

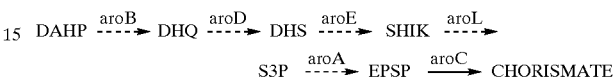

In strains containing pCL101EA, the natural rate-limitation at the aroB step (and any other steps within the common trunk of the aromatic amino acid pathway) is relieved, allowing unimpeded flow of carbon from DAHP to chorismate. The chorismate thus formed is converted by the endogenous (chromosomally encoded) E. coli pheA, tyrA and tyrB gene products to phenylalanine and tyrosine. This allows carbon commitment to the aromatic amino acid pathway to be measured as overall production of phenylalanine and tyrosine. Four strains were compared for phenylalanine and tyrosine production:

| Strain | Pts Phenotype | Cloned Gene(s) on Plasmids |
| --- | --- | --- |
| PB103/pRW5, pCL101EA | Pts⁺ | aroG, aroACBLE |
| PB103/pRW5tkt, pCL101EA | Pts⁺ | aroG + tktA, aroACBLE |
| NF9/pRW5, pCL101EA | Pts⁻/glucose⁺ | aroG, aroACBLE |
| NF9/pRW5tkt, pCL101EA | Pts⁻/glucose⁺ | aroG + tktA, aroACBLE |

The strains were grown with shaking in 30-ml flask cultures at 37° C. The medium used was YE medium, which contains (per liter of distilled water): 15 g yeast extract, 14 g $K_2HPO_4$, 16 g $KH_2PO_4$, 5 g $(NH_4)_2SO_4$, 15 g glucose, 1 g $MgSO_4$.7 H2O and 1 drop of P-2000 antifoam. Cultures were inoculated with cells from overnight seed cultures. The initial $OD_{660}$ of the cultures was 0.2. IPTG was added to the cultures (to induce high level expression of the aroG and aroACBLE genes) when the OD660 reached 2.0. The pH of the cultures was maintained at 6.5 throughout the experiment by periodic additions of 45% KOH Samples of the cultures were withdrawn at specified intervals, the cells removed by centrifugation, and the supernatant (cell-free culture broth) was analyzed by high performance liquid chromatography for the presence of phenylalanine, tyrosine and the common aromatic amino acid pathway intermediates.

The results shown in FIG. 6 show that the strains based on the Pts⁻/glucose⁺ host NF9 accumulated 2–3× more phenylalanine and 1.6× more tyrosine than their relevant control strains that were based on the Pts⁺ host PB103. Furthermore, in all cases, the presence of amplified transketolase activity (i.e., plasmid pRW5tkt) gave a 27–47% improvement in phenylalanine and tyrosine production. None of the strains accumulated detectable levels of the common aromatic amino acid pathway intermediates, illustrating the deblocking effect of plasmid pCL101EA.

These results show that carbon commitment to the aromatic amino acid pathway, measured as overall production of phenylalanine and tyrosine, is enhanced significantly in Pts⁻/glucose⁺ strains compared to their isogenic (Pts⁺) control strains.

EXAMPLE 8

In Examples 6 and 7 it was shown that the increase in intracellular PEP level in the Pts⁻/glucose⁺ strain NF9 (relative to its Pts⁺ parent strain PB103) can be translated into increased carbon commitment to the aromatic amino acid pathway. This increased carbon commitment was demonstrated as increased production of the first intermediate of the aromatic amino acid pathway, DAHP, and as increased production of two of the aromatic amino acids themselves, phenylalanine and tyrosine. In this example, it is shown that the increased carbon commitment to aromatics can also be translated into an increase in production of the third aromatic amino acid, tryptophan.

Three host strains were used in this experiment. PB103 (Pts⁺) and its Pts⁻/glucose⁺ derivative NF9 were described in Example 6. Strain JB102 (see Table 2a) is a serA mutant derived from PB103 and was included in this example because in separate experiments it has shown improved tryptophan performance compared to PB103 containing the same plasmids (unpublished).

Plasmid pBE7 (FIG. 7) confers tetracycline resistance and contains six cloned genes required for tryptophan production, aroG (encoding the first enzyme of the aromatic pathway, DAHP synthase) and the trpEDCBA genes (encoding the five enzymes of the tryptophan branch of the aromatic pathway). The trpE gene on pBE7 has been altered such that its product, anthranilate synthase, has been rendered resistant to feedback inhibition by tryptophan (trpE$^{fbr}$). Plasmid pBE6tkt (FIG. 8) is identical to plasmid pBE7 except that it specifies chloramphenicol resistance instead of tetracycline resistance, and also contains the cloned transketolase (tktA) gene, the function of the latter gene being to increase carbon commitment to aromatics by increasing the intracellular E4P supply (see Example 6). Plasmid pCL101EA, which confers spectinomycin resistance and is compatible with pBE7 or pBE6tkt, contains the aroACBLE genes (see Example 7) and functions to relieve rate-limiting steps in the common trunk of the aromatic pathway.

Four strains were compared for tryptophan production:

| Strain | Pts Phenotype | Relevant Cloned Gene(s) on Plasmids |
|---|---|---|
| PB103/pBE7 | Pts⁺ | aroG trpE$^{fbr}$ DCBA |
| NF9/pBE7 | Pts⁻/glucose⁺ | aroG trpE$^{fbr}$ DCBA |
| NF9/pBE7, pCL101EA | Pts⁻/glucose⁺ | aroG trpE$^{fbr}$ DCBA aroACBLE |
| JB102/pBE6tkt, pCL101EA | Pts⁺ | aroG tktA trpE$^{fbr}$ DCBA aroACBLE |

The strains were grown with shaking in 30-ml flask cultures at 37° C. The medium used was Amisoy medium, which contains (per liter of distilled water): 7 g Amisoy soy hydrolysate, 14 g $K_2HPO_4$, 16 g $KH_2PO_4$, 5 g $(NH_4)_2SO_4$, 15 g glucose, 1 g $MgSO_4$·7 $H_2O$, 0.27 g $FeCl_3$ and 1 drop of P-2000 antifoam. Cultures were inoculated with cells from overnight seed cultures grown in seed medium (identical to Amisoy medium except that 15 g of yeast extract is substituted for the 7 g of Amisoy and the $FeCl_3$ is omitted). The initial $OD_{660}$ of the cultures was 0.2. IPTG was added to the cultures at time zero to induce high level expression of the aroG, trpEDCBA and aroACBLE genes on the various plasmids (the tktA gene in plasmid pBE6tkt is under control of its native promoter). The pH of the cultures was maintained at 6.5 throughout the experiment by periodic additions of 45% KOH. Samples of the cultures were withdrawn at specified intervals, and mixed 1:1 with 95% ethanol. The cells and debris were removed by centrifugation, and the supernatant was analyzed for tryptophan, two intermediates specific to the tryptophan branch of the aromatic pathway (anthranilate and indole), and intermediates of the common trunk of the aromatic pathway (refer to Example 7), by high performance liquid chromatography.

The experimental results are shown in FIGS. 9a, 9b and 9c. There are three important comparisons to be made. First, the Pts⁻/glucose⁺ strain NF9/pBE7 produced 4.4× more tryptophan than its isogenic control strain PB103/pBE7 (FIG. 9a). NF9/pBE7 made only tryptophan, i.e., it did not accumulate significant levels of any of the common pathway intermediates or the tryptophan branch-specific intermediates anthranilate and indole. This result is consistent with the results presented in Examples 6 and 7.

Second, strain NF9/pBE7, pCL101EA produced 1.3× more tryptophan than NF9/pBE7 (which lacks the deblocking aroACBLE genes on pCL101EA) and 5.9× more tryptophan than PB103/pBE7 (which lacks both the Pts⁻/glucose⁺ mutation(s) and the aroACBLE genes) (FIG. 9a). Strain NF9/pBE7, pCL101EA also made almost exclusively tryptophan, with only a small accumulation of anthranilate being observed. These results are also consistent with those presented in Examples 6 and 7.

Third, in terms of total potential tryptophan produced, strain NF9/pBE7, pCL101EA performed almost identically to strain JB102/pBE6tkt, pCL101EA (FIG. 9b). The latter strain has been found to have markedly improved carbon flow through the aromatic amino acid pathway compared to appropriate control strains, owing to the presence of the combination of tkta and aroACBLE. However, the increased carbon flow in JB102/pBE6tkt, pCL101EA does not completely reach tryptophan; 55% is accumulated as anthranilate and indole (FIG. 9a). Since NF9/pBE7, pCL101EA made almost exclusively tryptophan, this strain is actually superior in this respect to the previous best strain JB102/pBE6tkt, pCL101EA. Because NF9/pBE7, pCL101EA made almost exclusively tryptophan, while JB102/pBE6tkt, pCL101EA co-accumulated tryptophan, anthranilate and indole, the specific tryptophan production rates for the two strains are only equivalent if tryptophan, anthranilate and indole are all considered for strain JB102/pBE6tkt, pCL101EA (FIG. 9c).

Like the results presented in Examples 6 and 7, the results presented in this example clearly show that the increased intracellular availability of PEP in Pts⁻/glucose⁺ strains enhances carbon commitment to the aromatic amino acid pathway compared to isogenic Pts⁺ control strains.

REFERENCES

1) M. Mori and I. Shio (1987) "Pyruvate formation and sugar metabolism in an amino acid-producing bacterium, *Brevibacterium flavum*" *Agric. Biol. Chem.* 51:129–138
2) J. Miller, K. Backman, M. O'Connor and R. Hatch (1987) "Production of phenylalanine and organic acids by phosphoenolpyruvate carboxylase-deficient mutants of *Escherichia coli*" *J. Ind. Microbiol.* 2:143–149
3) A. lida, S. Teshiba and K. Mizobuchi (1993) "Identification and characterization of the tktB gene encoding a second transketolase in *Escherichia coli* K-12" *J. Bacteriol.* 175:5375–5383

4) W. Holms (1986) "The central metabolic pathways of *Escherichia coli*: relationship between flux and control at a branch point, efficiency of conversion to biomass, and excretion of acetate" In: Current Topics in Cellular Regulation, Vol. 28, pp. 69–105, Academic Press, New York 5) K. M. Draths and J. W. Frost (1990) "Synthesis using plasmid-based catalysis: Plasmid assembly and 3-deoxy-D-arabino-heptulosonate production" J. Am. Chem. Soc. 112:1657–1659

6) P. W. Postma, J. W. Lengeler and G. R. Jacobson (1993) "Phosphoenolpyruvate carbohydrate phosphotransferase systems of bacteria" *Microbiol. Rev.* 57:543–594

7) A. Romano, J. Trifone and M. Brustolon (1979) "Distribution of the phosphoenolpyruvate:glucose phosphotransferase system in fermentative bacteria" *J. Bacteriol.* 139:93–97

8) M. Saier and M. Chin (1990) "Energetics of the bacterial phosphotransferase system in sugar transport and the regulation of carbon metabolism" In: Bacterial Energetics, pp. 273–299, T. A. Krulwich, ed., Academic Press, New York 9) A. Varma, B. W. Boesch and B. O. Palsson (1993) "Biochemical production capabilities of *Escherichia coli*" *Biotech. and Bioengin.* 42:59–73

10) J. Navas-Castillo, F. Laigret, A. Hocquellet, C. J. Chang and J. M. Bore (1993) "Evidence for a phosphoenolpyruvate dependent sugar-phosphotransferase system in the mollicute *Acholeplasma florum*" *Biochimie* (Paris) 75:675–679

11) E. Wagner, F. Gotz and R. Bruckner (1993) "Cloning and characterization of the scrA gene encoding the sucrose-specific enzyme II of the phosphotransferase system from *Staphylococcus xylosus*" *Mol Gen. Genet.* 241:33–41

12) N. D. Meadow, D. K. Fox and S. Roseman (1990) "The bacterial phosphoenolpyruvate:glycose phosphotransferase system" *Annu Rev. Biochem.* 59:497–542

13) Y.-Y. Chen, L. N. Lee and D. J. Leblanc (1993) "Sequence analysis of scrA and scrB from *Streptococcus sobrinus* 6715" *Infect Immun.* 61:2602–2610

14) M. Cocaign, C. Monnet and N. D. Lindley (1993) "Batch kinetics of *Corynebacterium glutamicum* during growth on various carbon substrates: use of substrate mixtures to localise metabolic bottlenecks" *Appl. Microbiol. and Biotechnol.* 40:526–530

15) K.-H. Yoon, S.-C. Park and T.-K. Oh (1993) "Cloning and characterization of the gene encoding enzyme II of the *Brevibacterium lactofermentum* phosphoenolpyruvate-dependent sugar phosphotransferase system" *Abstr. Ann. Meet Am. Soc. Microbiol.* 0–25

16) B. A. Degnan and G. T. MacFarlane (1993) "Transport and metabolism of glucose and arabinose in *Bifidobacterium breve*" *Arch. Microbiol.* 160:144–151

17) S. Chattopadhyay, A. Mukherjee and S. Ghosh (1993) "*Azospirillum brasilense* locus coding for phosphoenolpyruvate fructose phosphotransferase system and global regulation of carbohydrate metabolism" *J. Bacteriol.* 175:3240–3243

18) W. J. Mitchell, J. Riezer, C. Herring, C. Hoischen and M. H. Saier, Jr. (1993) "Identification of a phosphoenolpyruvate fructose phosphotransferase system (fructose 1-phosphate forming) in *Listeria monocytogenes*" *J. Bacteriol.* 175:2758–2761

19) S. Benthin, J. Nielsen and J. Villadsen (1993) "Transport of sugars via two anomer-specific sites on mannose-phosphotransferase system in *Lactococcus cremoris*: in vivo study of mechanism kinetics and adaptation" *Biotechnol. Bioeng.* 42:440–448

20) C. Yu, B. L. Bassler and S. Roseman (1993) "Chemotaxis of the marine bacterium *Vibrio fumissii* to sugars: a potential mechanism for initiating the catabolic cascade" *J. Biol. Chem.* 268:9405–9409

21) P. Henderson and M. Maiden (1990) "Homologous sugar transport proteins in *Escherichia coli* and their relatives in both prokaryotes and eukaryotes" *Phil. Trans. R. Soc.*, London 326:391–410

22) M. Weickert and S. Adhya (1993) "The galactose regulon of *Escherichia coli*" *Molecular Microbiol.* 10:245–251

23) P. Postma (1987) "Phosphotransferase system for glucose and other sugars" In: *Escherichia coli* and *Salmonella typhimurium*, Cellular and Molecular Biology, pp. 127–141, (F. Neidhart, J. Ingram, K. Low, M. Schaechter and H. Umbarger, ed.) ASM Publications, Washington, D.C.

24) F. Biville, E Turlin and F. Gasser (1991) "Mutants of *Escherichia coli* producing pyrroloquinoline quinone" *J. Gen. Microbiol.* 137:1775–1782

25) M. Saier, F. Bromberg and S. Roseman (1973) "Characterization of constitutive galactose permease mutants in *Salmonella typhimurium*" *J. Bacteriol.* 113:512–514

26) T. Silhavy, M. Berman and L. Enquist (1984) In: Experiments with Gene Fusions, pp. 110–112, Cold Springs Harbor Laboratory, New York 27) S. Levy, G. Zeng and A. Danchin (1990) "cAMP synthesis in strains bearing well characterized deletions in the central pts genes of *Escherichia coli*" Gene 86:27–33

28) C. Cordaro, T. Melton, J. Stratis, M. Atagun, C. Gladding, P. Hartman and S. Roseman (1976) "Fosfomycin resistance: selection method for internal and extended deletions of the phosphoenolpyruvate:sugar phosphotransferase genes of *Salmonella typhimurium*" *J. Bacteriol.* 128:785–793

29) D. Dykhuizen and D. Hartl (1983) "Selection in chemostats" *Microbiol Rev.* 47:150–168

30) C. Yanisch-Perron, J. Vieira and J. Messing (1985) "Improved M13 phage cloning vectors and host strains: nucleotide sequence of the M13mp18 and pUC19 vectors" Gene 33:103–119

31) M. J. Weickert and S. Adhya (1993) "Control of transcription of gal repressor and isorepressor genes in *Escherichia coli*" *J. Bacteriol.* 175:251–258

32) J. Sambrook, E. Fritch and T. Maniatis (1989) In: Molecular Cloning, A Laboratory Manual, 2nd Edition, Cold Springs Harbor Laboratory, New York 33) D. Mascarenhas (1987) "Tryptophan producing microorganism" PCT/WO87/01130

34) K. Backman, M. Ptashne and W. Gilbert (1976) "Construction of plasmids carrying the cl gene of bacteriophage λ" *Proc. Natl. Acad. Sci.* 73:4174–4178

35) P. R. Srinivasan and D. B. Sprinson (1959) "2-keto-3-deoxy-D-arabo-heptonic acid 7-phosphate synthetase" *J. Biol. Chem.* 234:716–722

What is claimed is:

1. A mutant host cell having a metabolic pathway which uses PEP as a precursor or intermediate of metabolism, said host cell characterized by:
(a) being phenotypically Pts–/glu+ wherein the Pts– phenotype is caused by the deletion or inactivation of all or substantially all of a gene selected from the group consisting of ptsl, ptsH and crr;
(b) requiring galactose permease activity to transport glucose; and (c) having a specific growth rate on glucose as a sole carbon source of at least 0.4 h$^{-1}$.

2. A mutant host cell of claim 1 comprising recombinant DNA coding for one or more of the enzymes selected from the group consisting of transketolase, transaldolase and phosphoenolpyruvate synthase such that the mutant host cell expresses transketolase, transaldolase or phosphoenolpyruvate synthase at enhanced levels relative to wild-type host cells.

3. A mutant host cell of claim 1 further comprising mutations in the pykA and/or pykF genes in said host cell.

4. A mutant host cell of claim 2 further comprising mutations in the pykA and/or pykF genes in said host cell.

5. A method for increasing PEP availability to a biosynthetic or metabolic pathway of a host cell, the method comprising, a) obtaining a host cell mutant characterized by having a Pts-/glu+ phenotype requiring galactose permease activity to transport glucose; and having a specific growth rate on glucose as a sole carbon source of at least 0.4 h$^{-1}$ wherein the Pts- phenotype is caused by the deletion or inactivation of all or substantially all of one of the genes b) selected from the group consisting of ptsl, ptsH and crr, and b) culturing the host cell mutant in the presence of an appropriate carbon source, wherein said host cell mutant utilizes PEP as a precursor or intermediate of metabolism.

6. A method of claim 5 further comprising modifying the host cell mutant to introduce therein recombinant DNA coding one or more of the enzymes selected from the group consisting of transketolase, transaldolase and phosphoenolpyruvate synthase such that the mutant host cell expresses transketolase, transaldolase or phosphoenolpyruvate synthase at enhanced levels relative to wild-type host cells.

7. The method of claim 5 further comprising modifying the host cell mutant to reduce or eliminate pyruvate kinase activity in said host cell.

8. A method of claim 7 wherein pyruvate kinase activity is reduced or eliminated in the host cell by introducing a mutation in DNA encoding one or more of the sequences coding for pyruvate kinase, pyruvate kinase promoter region and other regulatory sequences controlling expression of pyruvate kinase.

9. A method for obtaining a Pts-/Glucose$^+$, galactose permease requiring-mutant cell, the method comprising:

(a) selecting a host cell which utilizes a phosphotransferase transport system;

(b) mutating the host cell whereby the phosphotransferase transport system is inactivated;

(c) culturing the mutant host cell under continuous culture conditions using glucose as a carbon source; and (d) selecting mutant host cells which grow on glucose at a specific growth rate of at least 0.4 h$^{-1}$.

10. The method of claim 9 wherein said inactivating is by deleting part or all of gene(s) selected from the group consisting of ptsl, ptsH and crr.

11. The method of claim 9, wherein the selected mutant host cell has a specific growth rate of at least 50% of the host cell of step a).

12. A method for obtaining a Pts-/Glucose$^+$, galactose permease requiring-mutant cell, the method comprising:

(a) selecting a host cell which utilizes a phosphotransferase transport system;

(b) mutating the host cell whereby the phosphotransferase transport system is inactivated;

(c) culturing the mutant host cell using glucose as a carbon source; and (d) selecting mutant host cells having a specific growth rate on glucose of about 0.8 h$^{-1}$.

13. A mutant host cell having a metabolic pathway which uses PEP as a precursor or intermediate of metabolism, said host cell characterized by:

(a) being phenotypically Pts-/Glu$^+$;

(b) requiring galactose permease activity to transport glucose; and (c) having a specific growth rate on glucose as a sole carbon source of about 0.8 h$^{-1}$.

14. The mutant host cell of claim 13 further comprising mutations in a gene selected from the group pykA and pykF.

15. The mutant host cell of claim 13 further comprising recombinant DNA coding for one or more of the enzymes selected from the group consisting of transketolase, transaldolase, and phosphoenolpyruvate synthase wherein the mutant host cell expresses transketolase, transaldolase or phosphoenolpyruvate synthase at enhanced levels relative to wild-type host cells.

16. A method for enhancing production of a desired compound in a modified host cell, said host cell in its unmodified form being capable of utilizing a phosphotransferase transport system for carbohydrate transport, the method comprising, (a) obtaining a modified host cell, wherein said modified host cell is characterized by having
(i) a Pts-/glu+ phenotype;
(ii) requiring galactose permease activity to transport glucose;
(iii) having a specific growth rate on glucose as a sole carbon source of at least about 0.4 h$^{-1}$; and
(iv) utilizing PEP as a precursor or intermediate of metabolism, said modified host cell further comprising recombinant DNA encoding one or more enzyme(s) catalyzing reactions in the pathway of biosynthetic production of said desired compound in said modified host cell; and (b) culturing the modified host cell with an appropriate carbon source whereby the production of a desired compound in the modified host cell is enhanced compared to the production of said desired compound in the unmodified host cell.

17. The method of claim 16 wherein the Pts- phenotype is caused by the deletion or inactivation of all or substantially all of one or more gene(s) selected from the group consisting of ptsl, ptsH and crr.

18. The method of claim 16 further comprising recovering said desired compound.

19. A method of claim 16 wherein the DNA used to transform the host cell encodes one or more enzyme(s) selected from the group consisting of DAHP synthase, DHQ synthase, DHQ dehydratase, shikimate dehydrogenase, shikimate kinase, EPSP synthase and chorismate synthase.

20. A method of claim 16 further comprising transforming the host cell with recombinant DNA coding one or more enzyme(s) selected from the group consisting of transketolase, transaldolase and phosphoenolpyruvate synthase so that said enzyme is expressed at enhanced levels relative to wild-type host cells.

21. A method of claim 19 further comprising transforming the host cell with recombinant DNA coding one or more enzyme(s) selected from the group consisting of transketolase, transaldolase and phosphoenolpyruvate synthase so that said enzyme is expressed at enhanced levels relative to wild-type host cells.

22. A method of claim 16 wherein the desired compound is selected from the group consisting of tryptophan, tyrosine and phenylalanine.

23. A method of claim 22 wherein the desired compound is tryptophan and the host cell is transformed with DNA coding one or more gene(s) selected from the group consisting of aroG, aroA, aroC, aroB, aroL, aroE, trpE, trpD, trpC, trpB, trpA and tktA or tktB.

24. A method for enhancing production of a desired compound in a modified host cell, said host cell in its unmodified form being capable of utilizing a phosphotransferase transport system for carbohydrate transport, the method comprising, (a) obtaining a modified host cell, said modified host cell characterized by having
  (i) a Pts−/glu+ phenotype;
  (ii) requiring galactose permease activity to transport glucose;
  (iii) a specific growth rate on glucose as a sole carbon source of about 0.8 $h^{-1}$ and (iv) utilizing PEP as a precursor or intermediate of metabolism, said modified host cell further comprising recombinant DNA encoding one or more enzymes catalyzing reactions in the pathway of biosynthetic production of said desired compound in said modified host cell and (b) culturing the modified host cell with an appropriate carbon source whereby the production of a desired compound in the modified host cell is enhanced compared to the production of said desired compound in the unmodified host cell.

25. The method of claim 24 further comprising recovering said desired compound.

* * * * *